US012569414B2

(12) United States Patent
Herzog et al.

(10) Patent No.: US 12,569,414 B2
(45) Date of Patent: Mar. 10, 2026

(54) SUNSCREEN COMPOSITIONS CONTAINING POROUS METAL OXIDE SPHERES

(71) Applicant: BASF SE, Ludwigshafen am Rhein (DE)

(72) Inventors: Bernd Herzog, Grenzach-Wyhlen (DE); Brigitte Lindemann, Grenzach-Wyhlen (DE); Christian Cremer, Grenzach-Wyhlen (DE); Rupa Hiremath Darji, Tarrytown, NY (US); Liangliang Qu, Tarrytown, NY (US); Keith Task, Beachwood, OH (US)

(73) Assignee: BASF SE, Ludwigshafen am Rhein (DE)

( * ) Notice: Subject to any disclaimer, the term of this patent is extended or adjusted under 35 U.S.C. 154(b) by 672 days.

(21) Appl. No.: 17/437,986

(22) PCT Filed: Mar. 12, 2020

(86) PCT No.: PCT/EP2020/056628

§ 371 (c)(1),
(2) Date: Sep. 10, 2021

(87) PCT Pub. No.: WO2020/182936

PCT Pub. Date: Sep. 17, 2020

(65) Prior Publication Data

US 2022/0183934 A1 Jun. 16, 2022

(30) Foreign Application Priority Data

Mar. 12, 2019 (EP) .................................... 19162151

(51) Int. Cl.

| | |
|---|---|
| ***A61K 8/02*** | (2006.01) |
| ***A61K 8/25*** | (2006.01) |
| ***A61K 8/27*** | (2006.01) |
| ***A61K 8/29*** | (2006.01) |
| ***A61K 8/35*** | (2006.01) |
| ***A61K 8/368*** | (2006.01) |
| ***A61K 8/37*** | (2006.01) |
| ***A61K 8/41*** | (2006.01) |
| ***A61K 8/46*** | (2006.01) |
| ***A61K 8/49*** | (2006.01) |
| ***A61Q 17/04*** | (2006.01) |

(52) U.S. Cl.

CPC ............ *A61K 8/025* (2013.01); *A61K 8/0279* (2013.01); *A61K 8/25* (2013.01); *A61K 8/27* (2013.01); *A61K 8/29* (2013.01); *A61K 8/35* (2013.01); *A61K 8/368* (2013.01); *A61K 8/37* (2013.01); *A61K 8/415* (2013.01); *A61K 8/466* (2013.01); *A61K 8/4946* (2013.01); *A61K 8/4966* (2013.01); *A61K 8/4973* (2013.01); *A61Q 17/04* (2013.01); *A61K 2800/412* (2013.01); *A61K 2800/43* (2013.01); *A61K 2800/522* (2013.01); *A61K 2800/524* (2013.01); *A61K 2800/614* (2013.01); *A61K 2800/651* (2013.01)

(58) Field of Classification Search

CPC ........ A61K 8/025; A61K 8/0279; A61K 8/25; A61K 8/27; A61K 8/29; A61K 8/35; A61K 8/368; A61K 8/37; A61K 8/415; A61K 8/466; A61K 8/4966; A61K 8/4973; A61K 2800/412; A61K 2800/43; A61K 2800/522; A61K 2800/524; A61K 2800/614; A61K 2800/651; A61Q 17/04

See application file for complete search history.

(56) References Cited

U.S. PATENT DOCUMENTS

| | | | | |
|---|---|---|---|---|
| 7,344,706 | B2 * | 3/2008 | Haase .................. | A61K 8/4966 424/59 |
| 10,123,950 | B2 | 11/2018 | Mansouri et al. | |
| 2016/0143831 | A1 | 5/2016 | Brock et al. | |
| 2016/0206527 | A1 * | 7/2016 | Hueber .................. | A61K 8/064 |
| 2017/0027828 | A1 | 2/2017 | Lee et al. | |
| 2022/0015996 | A1 | 1/2022 | Watanabe et al. | |

FOREIGN PATENT DOCUMENTS

| | | | |
|---|---|---|---|
| CN | 107519028 | A | 12/2017 |
| EP | 1421931 | A2 | 5/2004 |
| EP | 2337546 | B1 | 3/2017 |
| EP | 3421097 | * | 2/2019 |
| JP | 2016-503006 | A | 2/2016 |
| JP | 2016-523938 | A | 8/2016 |
| JP | 2017190299 | * | 10/2017 |
| JP | 2017190299 | A * | 10/2017 |
| JP | 2020-090468 | A | 6/2020 |
| KR | 10-2009-0056658 | A | 6/2009 |
| WO | 93/11742 | A1 | 6/1993 |
| WO | 2014/097972 | A1 | 6/2014 |
| WO | 2014/203913 | A1 | 12/2014 |

OTHER PUBLICATIONS

JP 2017190299 English.*
International Search Report and Written Opinion received for PCT Patent Application No. PCT/EP2020/056628, mailed on Jun. 2, 2020, 11 pages.
European Search Report for EP Patent Application No. 19162151.5, Issued on Sep. 17, 2019, 3 pages.
International Preliminary Report on Patentability received for PCT Patent Application No. PCT/EP2020/056628, mailed on Sep. 23, 2021, 9 pages.
Sayre et al., "A comparison of in vivo and in vitro testing of sunscreening formulas", Photochemistry and Photobiology, vol. 29, Issue 3, Mar. 1979, pp. 559-566.
"Silica Nylon Powder", Sunjin Chemical, Sunsil 130 Series, Jul. 20, 2003, pp. 1-3.

* cited by examiner

*Primary Examiner* — Shirley V Gembeh
(74) *Attorney, Agent, or Firm* — Faegre Drinker Biddle & Reath LLP

(57) ABSTRACT

The present invention relates to a method for increasing sun protection factor (SPF) of a sunscreen composition, use of porous metal oxide spheres (e.g., microspheres) for increasing SPF of a sunscreen composition and preparation of sunscreen compositions comprising the porous spheres.

15 Claims, 14 Drawing Sheets

SUNSCREEN COMPOSITIONS CONTAINING POROUS METAL OXIDE SPHERES

CROSS-REFERENCE TO RELATED APPLICATIONS

This application is a national stage application (under 35 U.S.C. § 371) of PCT/EP2020/056628, filed Mar. 12, 2020, which claims benefit of European Application No. 19162151.5, filed Mar. 12, 2019, both of which are incorporated herein by reference in their entirety.

The present invention relates to a method for increasing sun protection factor (SPF) of a sunscreen composition, use of porous metal oxide spheres for increasing SPF of a sunscreen composition and preparation of sunscreen compositions comprising the porous spheres.

Sunscreen compositions are used to shield human skin from the damage of solar radiations. Sunscreen compositions having high UV protection (high SPF) are required to prevent adverse effects of solar radiations, particularly those of the UV radiations. Wide varieties of UV absorbers are available for use in sunscreen compositions.

However, challenges still exist for providing sunscreen compositions having high SPF because of the restriction for incorporating high amounts of UV filters in cosmetic compositions due to various reasons such as their low solubility or regulatory restrictions. Additionally, such compositions may be associated with problems such as whitening effect. Therefore, there is a need for methods to increase the SPF of existing sunscreen compositions while maintaining their transparency.

Accordingly, it is an object of this invention to provide a method for increasing SPF of a sunscreen composition. Further, it is required that the sunscreen composition is not associated with adverse appearance problems such as whitening effect.

SUMMARY OF THE INVENTION

Surprisingly, it has been found that the object can be achieved by addition of porous spheres (e.g., microspheres) comprising a metal oxide to a sunscreen composition, which increases the SPF of the sunscreen composition.

Accordingly, the main aspect of the presently claimed invention is to provide a method for increasing the SPF of a sunscreen composition. The method comprises adding porous spheres (e.g., microspheres) comprising a metal oxide to the sunscreen composition, wherein the metal oxide is at least one selected from the group consisting of silica, titania, alumina, zirconia, ceria, iron oxides, zinc oxide, indium oxide, tin oxide and chromium oxide.

Another aspect of the presently claimed invention is a use of porous spheres (e.g. microspheres) comprising a metal oxide for increasing the sun protection factor of a sunscreen composition, wherein the metal oxide is at least one selected from the group consisting of silica, titania, alumina, zirconia, ceria, iron oxides, zinc oxide, indium oxide, tin oxide and chromium oxide.

In yet another aspect, the presently claimed invention provides a sunscreen composition comprising water and the porous spheres (e.g., microspheres) comprising a metal oxide in the range of 0.1 to 10.0 weight-%, based on total weight of the sunscreen composition, wherein the metal oxide is at least one selected from the group consisting of silica, titania, alumina, zirconia, ceria, iron oxides, zinc oxide, indium oxide, tin oxide and chromium oxide.

BRIEF DESCRIPTION OF THE DRAWINGS

The disclosure described herein is illustrated by way of example and not by way of limitation in the accompanying figures.

DETAILED DESCRIPTION

Figure 1:
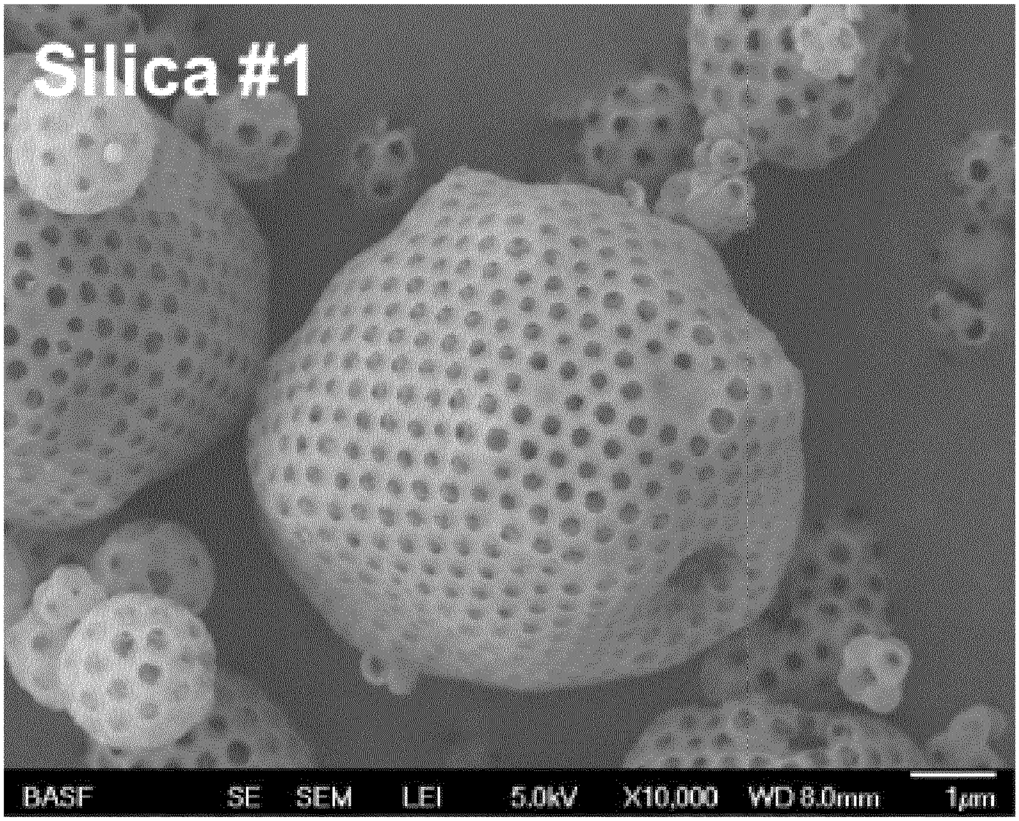
FIG. 1 is a scanning electron microscope (SEM) image of a porous silica sphere, according to an embodiment of the invention.

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms ‘first’, ‘second’, ‘third’ or ‘a’, ‘b’, ‘c’, etc. and the like in the description and in the claims, are used for distinguishing between similar elements and not necessarily for describing a sequential or chronological order. It is to be understood that the terms so used are interchangeable under appropriate circumstances and that the embodiments of the presently claimed invention described herein are capable of operation in other sequences than described or illustrated herein. In case the terms 'first', 'second', 'third' or '(A)', '(B)' and '(C)' or '(a)', '(b)', '(c)', '(d)', 'i', 'ii' etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

Furthermore, the ranges defined throughout the specification include the end values as well i.e. a range of 1 to 10 implies that both 1 and 10 are included in the range. For the avoidance of doubt, applicant shall be entitled to any equivalents according to applicable law.

In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment, but may.

Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination.

Surprisingly, it has been found that the addition of porous spheres (e.g., microspheres) comprising a metal oxide to a sunscreen composition results in an increase the SPF of the sunscreen composition. Further, it is observed that the resultant sunscreen composition does not show the whitening effect usually associated with the addition of scattering particles. As a result, the presently claimed invention provides sunscreen compositions having a high SPF and a low whitening.

The porous metal oxide spheres (e.g., microspheres) scatter the light passing through a sunscreen composition. As a result, the presence of porous metal oxide spheres (e.g., microspheres) in a sunscreen composition leads to an overall increase in the pathlength of the light travelling through the sunscreen layer. Consequently, the photon absorption by the UV filter or dye molecules present in the sunscreen composition increases. Thus, an overall increase in absorbance of the dye or the UV absorber is achieved without increasing its concentration.

Accordingly, the main aspect of the presently claimed invention is to provide a method for increasing the sun protection factor of a sunscreen composition. The method comprises adding porous spheres (e.g., microspheres) comprising a metal oxide to the sunscreen composition, wherein the metal oxide is preferably at least one selected from the group consisting of silica, titania, alumina, zirconia, ceria, iron oxides, zinc oxide, indium oxide, tin oxide and chromium oxide.

In certain embodiments, the metal oxide is at least one selected from the group consisting of silica, zinc oxide and titania. In another embodiment, the metal oxide is silica. In yet another embodiment is titania.

Another aspect of the presently claimed invention is use of porous spheres (e.g., microspheres) comprising a metal oxide for increasing the sun protection factor of a sunscreen composition, wherein the metal oxide is preferably at least one selected from the group consisting of silica, titania, alumina, zirconia, ceria, iron oxides, zinc oxide, indium oxide, tin oxide and chromium oxide.

In certain embodiments the metal oxide is at least one selected from the group consisting of silica, zinc oxide and titania. In another embodiment, the metal oxide is silica. In yet another embodiment, the metal oxide is titania.

In certain embodiments, the porous spheres (e.g., microspheres) comprise an additional light absorber. In a preferred embodiment, the additional light absorber is carbon black powder. In the context of the present invention, microspheres are spherical or spherical-like microparticles with average diameter or particle size typically ranging from 1 μm to 1000 μm (1 mm). Examples of microspheres include glass microspheres and polyethylene microspheres.

In the context of the present invention, the SPF factor (sun protection factor, SPF) serves to evaluate light protection preparations (sunscreen compositions) on humans (in vivo). It indicates how much longer a person with a sunscreen agent can be exposed to the sun without suffering sunburn than would be possible with the particular individual's self-protection time.

The SPF is determined in vitro by measuring the diffuse transmission in the spectral range between 290 and 400 nm.

In the context of the present invention, the term "monodisperse" in reference to spheres, microspheres or nanospheres means particles having generally uniform shapes and generally uniform diameters. A present monodisperse population of spheres, microspheres or nanospheres may have 90%, 91%, 92%, 93%, 94%, 95%, 96%, 97%, 98% or 99% of the particles by number having diameters within ±7%, ±6%, ±5%, ±4%, ±3%, ±2% or ±1% of the average diameter of the population.

In the context of the present invention, the term "particle size" is synonymous with particle diameter and is determined for instance with scanning electron microscopy (SEM) or transmission electron microscopy (TEM). Average particle size is synonymous with D50, meaning half of the population resides above this point, and half below. Particle size refers to primary particles. Particle size may be measured by laser light scattering techniques, with dispersions or dry powders.

In certain embodiments, the porous spheres (e.g., microspheres) are present in an amount in the range of 0.1 to 10.0 weight-%, or in the range of 1.0 to 8.0 weight-%, or in the range of 2.0 to 7.0 weight-%, based on total weight of the sunscreen composition.

In a particularly preferred embodiment, the porous spheres (e.g., microspheres) are present in an amount of 5.5 weight-%, based on total weight of the sunscreen composition.

In another particularly preferred embodiment, the porous spheres (e.g., microspheres) are present in an amount of 2.0 weight-%, based on total weight of the sunscreen composition.

In certain embodiments, the amount of the metal oxide in the porous spheres is in the range of 60.0 to 99.9 weight-%, or in the range of 65.0 to 99.0 weight-%, or in the range of 75.0 to 98.0 weight-% or in the range of 80.0 to 95.0 weight-%, based on total weight of the porous spheres.

In certain embodiments, the porous spheres have an average diameter in the range of 0.5 μm to 100.0 μm; or in the range of 1.0 μm to 90.0 μm; or in the range of 5.0 μm to 80.0 μm; or in the range of 10.0 μm to 70.0 μm; or in the range of 20.0 μm to 50.0 μm.

In certain embodiments, the porous spheres have an average porosity in the range of 0.10 to 0.90.

In certain embodiments, the porous spheres have an average porosity in the range of 0.10 to 0.80, or in the range of 0.30 to 0.80; or in the range of 0.15 to 0.75; or in the range of 0.25 to 0.60; or in the range of 0.30 to 0.50.

In certain embodiments, the porous spheres are monodisperse.

In certain embodiments, the porous spheres have an average pore diameter in the range of 50 nm to 999 nm; or in the range of 100 nm to 900 nm; or in the range of 200 nm to 800 nm; or in the range of 300 nm to 700 nm; or in the range of 400 nm to 600 nm.

In certain embodiments, the porous spheres have more than one population of pores each having an average pore diameter, wherein each population has a different average pore diameter. In another embodiment, the porous spheres have two population of pores each having an average pore diameter.

In certain embodiments, the porous spheres a. have an average diameter in the range of 0.5 μm to 100.0 μm;
b. have an average porosity in the range of 0.10 to 0.90;
c. have an average pore diameter in the range of 50 nm to 999 nm and
d. are monodisperse.

In certain embodiments, the porous spheres a. have an average diameter in the range of 0.5 μm to 100.0 μm;
b. have an average porosity in the range of 0.10 to 0.80;
c. have an average pore diameter in the range of 50 nm to 999 nm; and
d. are monodisperse.

In certain embodiments, the porous metal oxide spheres are prepared using a polymeric sacrificial template.

The porous spheres are prepared, e.g., by a method comprising the following steps.

A liquid dispersion of polymer particles (e.g., nanoparticles) and a metal oxide is formed. Liquid droplets of the dispersion are formed. The liquid droplets are dried to provide polymer template spheres (e.g., microspheres) comprising polymer spheres and metal oxide. The polymer spheres are removed from the template spheres to provide the porous metal oxide spheres.

Another method for the preparation of the porous spheres having at least two different average particle sizes comprises the following steps.

A liquid solution or dispersion of monodisperse polymer particles (e.g., nanoparticles) is formed. At least one further liquid solution or dispersion of monodisperse polymer particles (e.g., nanoparticles) is formed. The average diameters of the monodisperse polymer particles of each of the solutions or dispersions are different.

Each of the solutions or dispersions are mixed together; wherein a metal oxide is added to one or more of the solutions or dispersions and/or wherein a metal oxide is added to the mixture, to obtain a final liquid dispersion of polymer particles and a metal oxide.

Liquid droplets of the final liquid dispersion are formed. The liquid droplets are dried to provide polymer template spheres comprising monodisperse polymer spheres having bimodal distribution and the metal oxide. The polymer spheres are removed from the template spheres to provide the porous metal oxide spheres which are typically microspheres.

In certain embodiments, the method comprises forming a liquid dispersion of polymer particles (e.g., nanoparticles) and the metal oxide, spray-drying the liquid dispersion to provide polymer template spheres and removing the polymer spheres from the template spheres.

The liquid droplets are aqueous droplets or oil droplets. In certain embodiments, a vibrating nozzle is employed for the formation the liquid droplets.

In certain embodiments, the method comprises providing a continuous phase and mixing the liquid dispersion with the continuous phase to form an emulsion containing dispersed liquid dispersion droplets and collecting the droplets.

In certain embodiments, the drying involves microwave irradiation, oven drying, drying under vacuum, drying in the presence of a desiccant, or a combination thereof.

In certain embodiments, a weight ratio of the polymer particles (e.g., nanoparticles) to the metal oxide is in the range of 0.5:1 to 10.0:1.

In certain embodiments, the polymer is selected from the group consisting of poly(meth)acrylic acid, poly(meth)acrylates, polystyrenes, polyacrylamides, polyethylene, polypropylene, polylactic acid, polyacrylonitrile, derivatives thereof, salts thereof, copolymers thereof and combinations thereof.

In certain embodiments, the polymer spheres (e.g., nanospheres) are removed from the template spheres (e.g., microspheres) using techniques such as calcination, pyrolysis or solvent removal.

In certain embodiments, the polymer spheres (e.g., nanospheres) are removed from the template spheres (e.g., microspheres) by calcining the template spheres at temperatures in the range of 350 to 700° C. for a period of 1 to 8 hours.

The porous spheres (e.g., microspheres) comprising a metal oxide are spherical or spherical-like and are micron-scaled.

The polymer particles employed as template are spherical, nano-scaled and are monodisperse. The metal oxide employed may also be in particle form and having nano-scaled particles. Drying of the polymer/metal oxide droplets followed by removal of the polymer provides microspheres having uniform voids (pores). Thus, the porous metal oxide spheres contain uniform pore diameters as a result of the polymer particles being porous and monodisperse.

The pore diameters are dependent on the size of the polymer particles. Some shrinkage or compaction may occur upon polymer removal, providing pore sizes somewhat smaller than the original polymer particle size, for example from 10% to 40% smaller than the polymer particle size. The pore diameters are uniform as are the polymer particle shape and size.

UV Absorbers

In certain embodiments, the sunscreen composition further comprises an UV absorber selected from the group consisting of ($d_1$) p-aminobenzoic acid derivatives;
($d_2$) salicylic acid derivatives;
($d_3$) benzophenone derivatives;
($d_4$) dibenzoylmethane derivatives;

($d_5$) diphenyl acrylates;
($d_6$) 3-imidazol-4-yl-acrylic acid and its esters;
($d_7$) benzofuran derivatives;
($d_8$) polymeric UV absorbers;
($d_9$) cinnamic acid derivatives;
($d_{10}$) camphor derivatives;
($d_{11}$) hydroxyphenyltriazine derivatives;
($d_{12}$) benzotriazole derivatives;
($d_{13}$) trianilino-s-triazine derivatives;
($d_{14}$) 2-phenylbenzimidazole-5-sulfonic acid and salts thereof;
($d_{15}$) menthyl o-aminobenzoates;
($d_{16}$) homosalates;
($d_{17}$) tris-biphenyltriazine derivatives;
($d_{19}$) $TiO_2$ (partly encapsulated), ZnO and mica;
($d_{19}$) benzylidenemalonates;
($d_{20}$) merocyanine derivatives;
($d_{21}$) phenylene bis diphenyltriazines;
($d_{22}$) imidazoline derivatives; and
($d_{23}$) diarylbutadiene derivatives.

Compounds which can be employed by way of example for p-aminobenzoic acid derivatives ($d_1$) are 4-aminobenzoic acid (PABA); ethyldihydroxypropyl-PABA of the formula (PABA-01)

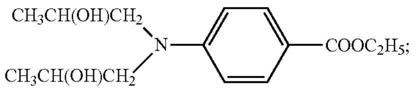

PEG-25-PABA of the formula (PABA-02)

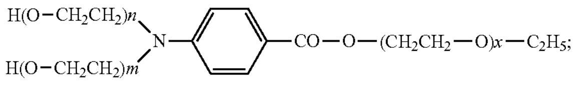

wherein m, n and x have the same meaning and each denote at most 25; octyldimethyl PABA of the formula (PABA-03)

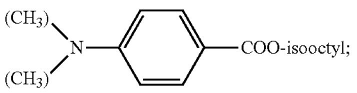

or glycyl aminobenzoate of the formula (PABA-04)

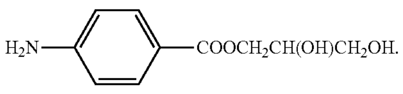

Compounds which can be employed by way of example for salicylic acid derivatives ($d_2$) are homomenthyl salicylate of the formula (SAD-01)

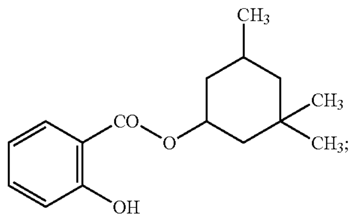

triethanolamine salicylate of the formula (SAD-02)

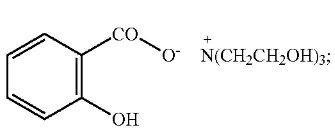

amyl p-di-methylaminobenzoate of the formula (SAD-03)

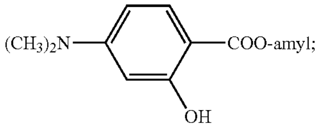

octyl salicylate of the formula (SAD-04)

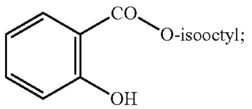

or 4-isopropylbenzyl salicylate of the formula (SAD-05)

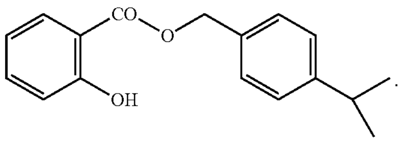

Compounds which can be employed by way of example for benzophenone derivatives ($d_3$) are:

benzophenone-3 (2-hydroxy-4-methoxybenzophenone); benzophenone-4 (2-hydroxy-4-methoxybenzophenone-5-sulfonic acid); benzophenone-8 (2,2'-dihydroxy-4-methoxy-benzo-phenone); or amino-substituted hydroxybenzophenones of the formula (HBP-01)

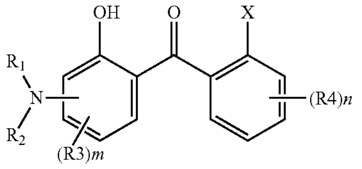

wherein $R_1$ and $R_2$ denote hydrogen, $C_1$-$C_{20}$-alkyl, $C_2$-$C_{10}$-alkenyl, $C_3$-$C_{10}$-cycloalkyl, $C_3$-$C_{10}$-cycloalkenyl, wherein the substituents $R_1$ and $R_2$ together with the nitrogen atom to which they are bonded can form a 5- or 6-membered ring;

$R_3$ and $R_4$ independently of each other denote $C_1$-$C_{20}$-alkyl; $C_2$-$C_{10}$-alkenyl; $C_3$-$C_{10}$-cycloalkyl;

$C_3$-$C_{10}$-cycloalkenyl; $C_1$-$C_{22}$-alkoxy; $C_1$-$C_{20}$-alkoxycarbonyl; $C_1$-$C_{12}$-alkylamino; $C_1$-$C_{12}$-dialkylamino; optionally substituted aryl; hetaryl; substituents conferring solubility in water selected from the group consisting of a nitrile group, and carboxylate, sulfonate or ammonium radicals;

X denotes hydrogen; $COOR_5$; or $CONR_6R_7$;

$R_5$, $R_6$, $R_7$ independently of each other denote hydrogen; $C_1$-$C_{20}$-alkyl; $C_2$-$C_{10}$-alkenyl; $C_3$-$C_{10}$-cycloalkyl; $C_3$-$C_{10}$-cycloalkenyl; $(Y—O)_o—Z$; or aryl;

Z denotes $—CH_2—CH_3$; $—CH_2—CH_2—CH_3$; $—CH_2—CH_2—CH_2—CH_3$; or $—CH(CH_3)—CH_3$;

Dimeric benzophenone derivatives corresponding to the formula (HBP-03)

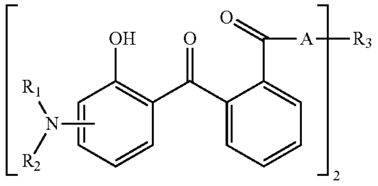

wherein $R_1$ and $R_2$ independently of each other denote $C_1$-$C_{20}$-alkyl; $C_2$-$C_{20}$-alkenyl; $C_3$-$C_{10}$-cycloalkyl; $C_3$-$C_{10}$-cycloalkenyl; or $R_1$ and $R_2$ together with the nitrogen atom to which they are bonded form a 5- or 6-membered heterocyclic ring;

$R_3$ denotes alkylene, cycloalkylene, alkenylene or phenylene optionally substituted by a carbonyl or carboxyl group; a biradical of the formula (HBP-03a) $*—CH_2—C≡C—CH_2—*$; or $R_3$ together with A forms a bivalent radical of the formula (HBP-03b)

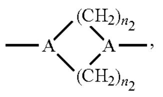

wherein $n_2$ denotes a number from 1 to 3;

A denotes —O—; or $—N(R_5)—$; and $R_5$ denotes hydrogen; $C_1$-$C_5$-alkyl; or hydroxy-$C_1$-$C_5$-alkyl;

can also be employed according to the invention.

In particular, dimeric benzophenone derivatives of the formula (HBP-04)

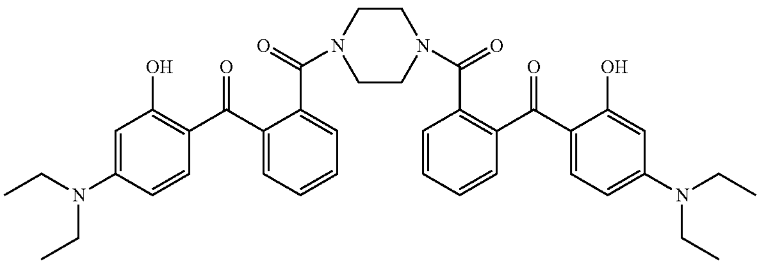

and (HBP-05)

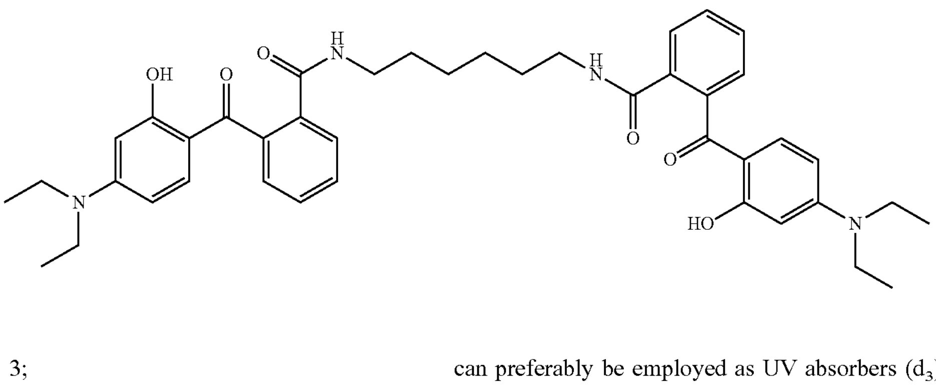

m denotes 0 to 3;

n denotes 0 to 4; and denotes 1 to 20.

In a most preferred embodiment, the UV absorber is 2-hydroxy-4-methoxybenzophenone-5-sulfonic acid.

can preferably be employed as UV absorbers ($d_3$).

Examples of dibenzoylmethane derivatives ($d_4$) which can be employed according to the invention are butyl-methoxydibenzoylmethane-[1-(4-tert-butylphenyl)-3-(4-methoxy-phenyl)propane-1,3-dione].

Examples of diphenylacrylate derivatives ($d_5$) which can be employed according to the invention are octocrylene-(2-ethylhexyl 2-cyano-3,3'-diphenylacrylate) or etocrylene (ethyl 2-cyano-3,3'-diphenylacrylate).

Examples of benzofuran derivatives ($d_7$) which can be employed according to the invention are 3-(benzofuranyl) 2-cyanoacrylate, 2-(2-benzofuranyl)-5-tert-butylbenzoxazole or 2-(p-aminophenyl)benzofuran and in particular the compounds of the formula (BF-01)

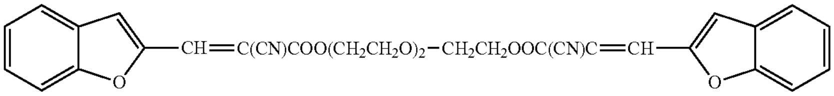

or (BF-02)

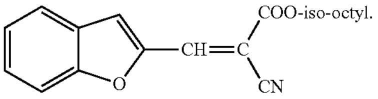

Examples of polymeric UV absorbers ($d_3$) which can be employed according to the invention and contain one or more organosilicon radicals are benzylidenemalonate derivatives, in particular the compound of the formula (PUV-01)

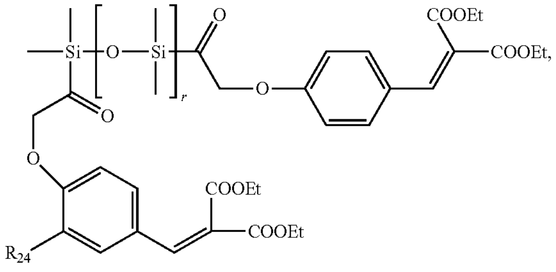

wherein $R_{24}$ denotes hydrogen or methoxy and r denotes approximately 7; the compound of the formula (PUV 02)

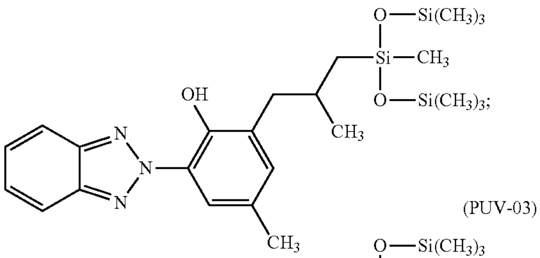

(PUV-03)

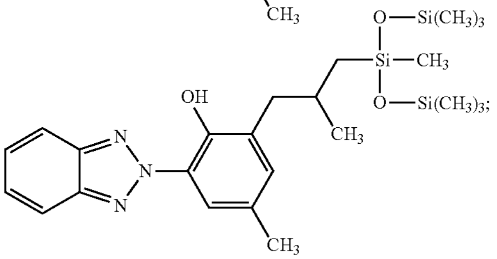

or polysilicone-15 corresponding to the formula (PUV-04)

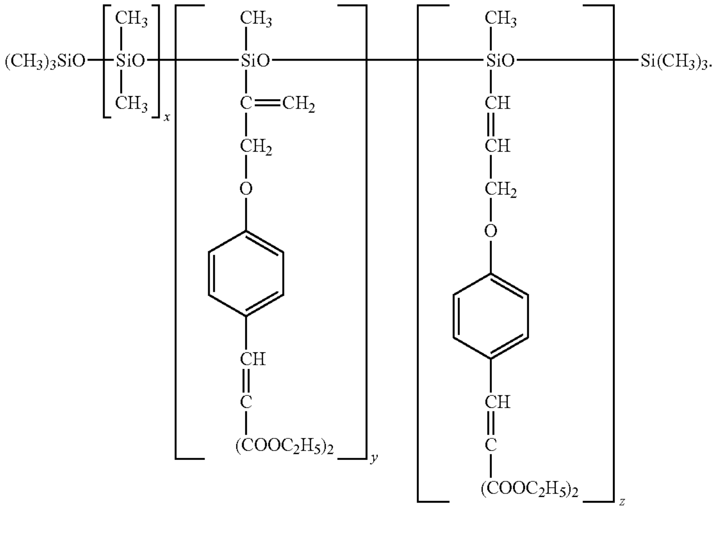

Examples of cinnamic acid esters ($d_9$) which can be employed according to the invention are octyl methoxycinnamate (4-methoxycinnamic acid 2-ethylhexyl ester), diethanolamine methoxycinnamate (diethanolamine salt of 4-methoxycinnamic acid), isoamyl p-methoxycinnamate (4-ethoxycinnamic acid 2-isoamyl ester), 2,5-diisopropyl methycinnamate or a cinnamic acid amido derivative.

Examples of camphor derivatives ($d_{10}$) which can be used according to the invention are 4-methylbenzylidenecamphor [3-(4'-methyl)benzylidenebornan-2-one], 3-benzylidenecamphor (3-benzylidenebornan-2-one), polyacrylamidomethylbenzylidenecamphor {N-[2(and 4)-2-oxyborn-3-ylidenemethyl)benzyl]acrylamide polymer}, trimoniumbenzylidenecamphor sulfate-[3-(4'-trimethylammonium)-benzylidenebornan-2-one methylsulfate], terephthalydenedicamphorsulfonic acid {3,3'-(1,4-phenylenedimethine)-bis-(7,7-dimethyl-2-oxobicyclo-[2.2.1]heptane-1-methanesulfonic acid} or salts thereof, or benzylidenecamphorsulfonic acid [3-(4'-sulfo)benzylidenebornan-2-one] or salts thereof.

Examples of hydroxyphenyltriazine derivatives ($d_{11}$) which can be used according to the invention are, in particular, bis-resorcinyltriazines of the formula (HPT-01)

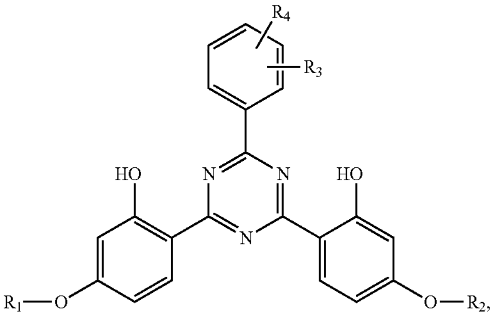

wherein $R_1$ and $R_2$ independently of each other denote hydrogen; $C_1$-$C_{18}$-alkyl; $C_2$-$C_{18}$-alkenyl; a radical of the formula $—CH_2—CH(—OH)—CH_2—O-T_1$; a radical of the formula (HPT-01a)

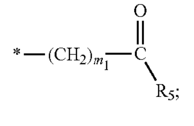

or a radical of the formula (HPT-01h)

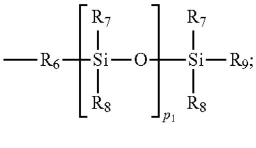

$R_3$, $R_4$ and $R_5$ independently of each other denote hydroxyl; $C_1$-$C_5$-alkoxy which is unsubstituted or substituted by one or more OH groups; amino; mono- or di-$C_1$-$C_5$-alkylamino; M; a radical of the formula (HPT-01b)

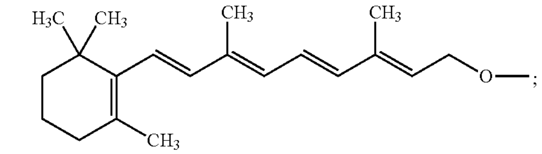

(HPT-01c)

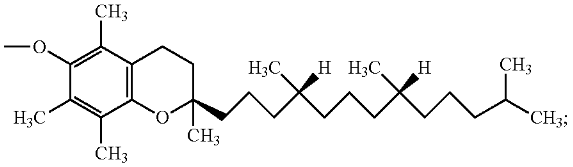

(HPT-01d)

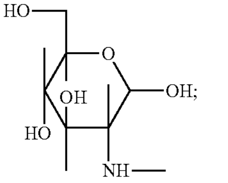

(HPT-01e)

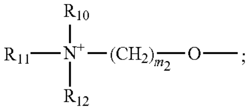

(HPT-01f)

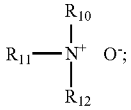

or (HPT-01g)

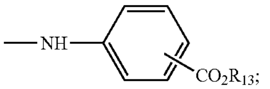

$R_{10}$, $R_{11}$ and $R_{12}$ independently of each other denote $C_1$-$C_{14}$-alkyl which is unsubstituted or substituted by one or more OH groups;

$R_{13}$ denotes hydrogen; M; $C_1$-$C_5$-alkyl; or a radical of the formula $—(CH_2)_{m3}—O-T_1$;

$R_6$ denotes the direct bond; a straight-chain or branched $C_1$-$C_4$-alkylene radical; or a radical of the formula $—C_{m4}H_{2m4}$, or $—C_{m4}H_{2m4}—O—$;

$R_7$, $R_8$ and $R_9$ independently of each other denote $C_1$-$C_{13}$-alkyl; $C_1$-$C_{18}$-alkoxy or a radical of the formula (HPT-01m)

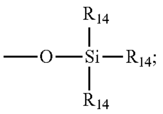

$R_{14}$ denotes $C_1$-$C_5$-alkyl;

M denotes a metal cation;

$T_1$ denotes hydrogen; or ($C_1$-$C_8$)-alkyl;

$m_1$, $m_2$ and $m_3$ independently of each other denote 1 to 3;

$m_4$ denotes 2 to 14; and $p_1$ denotes 0 or a number from 1 to 5.

Examples of representatives of the compound class ($d_{11}$) which may be mentioned are:

2-(4'-methoxyphenyl)-4,6-bis(2'-hydroxy-4'-n-octyloxyphenyl)-1,3,5-triazine;

2,4-bis{[4-(3-(2-propyloxy)-2-hydroxypropyloxy)-2-hydroxy]phenyl}-6-(4-methoxy-phenyl)-1,3,5-triazine;

2,4-bis{[4-(2-ethylhexyloxy)-2-hydroxy]phenyl}-6-[4-(2-methoxyethylcarboxyl)phenyl-amino]-1,3,5-triazine;

2,4-bis{[4-(tris(trimethylsiloxysilylpropyloxy)-2-hydroxy]phenyl}-6-(4-methoxyphenyl)-1,3,5-triazine;

2,4-bis{[4-(2"methylpropenyloxy)-2-hydroxy]phenyl}-6-(4-methoxyphenyl)-1,3,5-triazine;

2,4-bis{[4-(1',1',1',3',5',5',5'-heptamethyltrisilyl-2"-methyl-propyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-[4-ethylcarboxyl)phenylamino]-1,3,5-triazine;

2,4-bis{[4-(2-ethylhexyloxy)-2-hydroxy]phenyl}-6-(1-methylpyrrol-2-yl)-1,3,5-triazine; or 2,2'-[6-(4-methoxyphenyl)-1,3,5-triazine-2,4-diyl]bis[5-[(2-ethylhexypoxy]-(Bis-Ethylhexyloxyphenol Methoxyphenyl Triazine) corresponding to the formula (BRT-02)

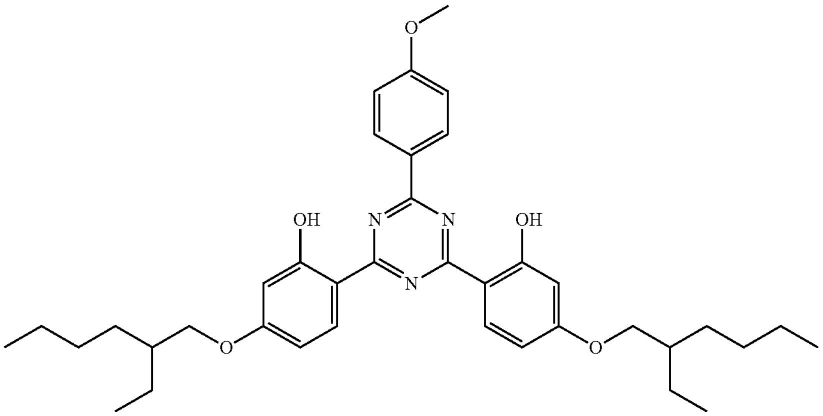

Examples of benzotriazole derivatives ($d_{12}$) which can be used according to the invention correspond to the formula (BT-01)

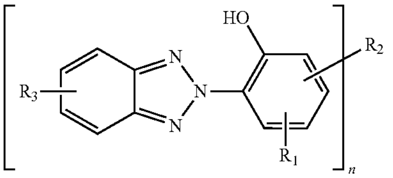

wherein $R_1$ denotes hydrogen; $C_1$-$C_{12}$-alkyl; $C_1$-$C_{12}$-alkoxy; $C_1$-$C_{12}$-alkoxycarbonyl; $C_5$-$C_{10}$-cycloalkyl or —$S0_3M$;

$R_3$ denotes hydrogen; $C_1$-$C_{18}$-alkyl; $C_1$-$C_{12}$-alkoxy; or halogen; and n denotes 1 or 2;

if n=1

$R_2$ denotes $C_1$-$C_{20}$-alkyl; $C_5$-$C_{10}$-cyclo-$C_1$-$C_5$-alkyl; $C_1$-$C_{12}$-alkoxy-$C_1$-$C_5$-alkyl; $C_5$-$C_{10}$-cyclo-alkoxy-$C_1$-$C_5$-alkyl; $C_6$-$C_{10}$-aryl; $C_6$-$C_{10}$-aryl-$C_1$-$C_5$-alkyl;

if n=2

$R_2$ denotes the direct bond; or —$(CH_2)_p$—; and p is an integer from 1 to 3.

Preferably, compounds of the formula (BT-01), wherein $R_1$ denotes $C_1$-$C_{12}$-alkyl; or —$S0_3M$;

$R_3$ denotes hydrogen; halogen, preferably Cl;

n denotes 1;

$R_2$ $C_1$-$C_{12}$-alkyl; and p denotes 1 to 3;

are possible.

Very particularly preferred compounds are those of the formula

BT-02

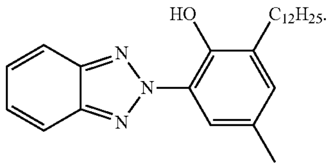

Furthermore, preferred UV filters of the formula BT-01 are those wherein $R_1$ denotes hydrogen;

$R_3$ denotes $C_1$-$C_{13}$-alkyl;

n=2; and $R_2$ denotes —$CH_2$—.

Very particularly preferred compounds are those of the formula (BT-03)

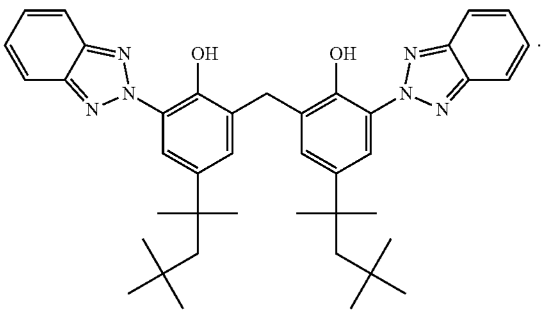

Examples of trianilino-s-triazine derivatives ($d_{13}$) which can be used according to the invention correspond to the formula (TAT-01)

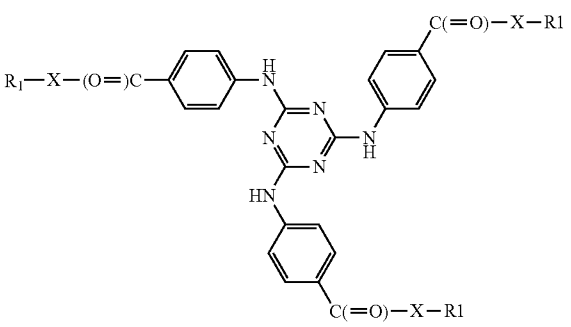

wherein $R_1$, $R_2$ and $R_3$ independently of each other denote optionally substituted $C_1$-$C_{20}$-alkyl, aryl or hetaryl;

X denotes O; or $NR_4$; and $R_4$ denotes hydrogen; or optionally substituted $C_1$-$C_{20}$-alkyl, aryl or hetaryl.

A particularly preferred representative of this compound class is Ethylhexyl Triazone corresponding to the formula (TAT-02)

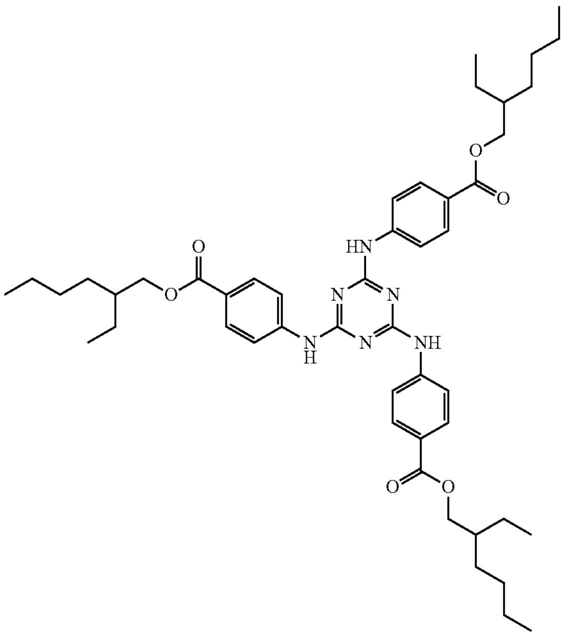

or Diethylhexyl Butamido Triazone corresponding to the formula (TAT-03)

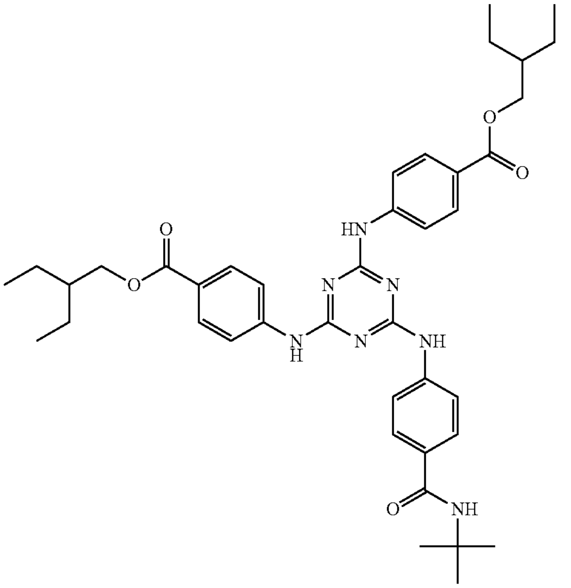

or Ethylhexyl Bis-Isopentylbenzoxazolylphenyl Melamine corresponding to the formula (TAT-04)

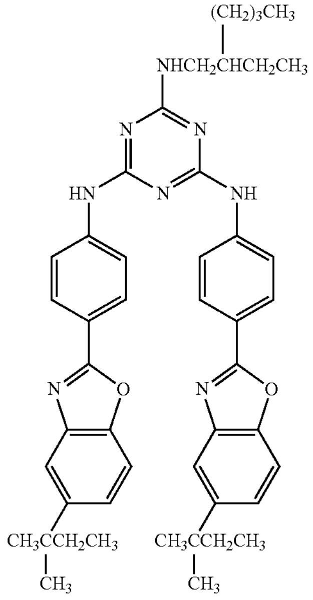

Preferred tris-biphenyl-triazine derivatives ($d_{17}$) which can be used according to the invention correspond to the formula (TBT-01)

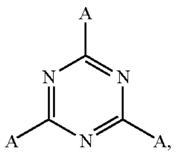

wherein

A denotes a radical of the formula (TBT-01a)

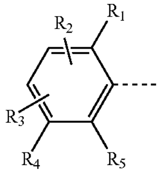

; or (TBT-01b)

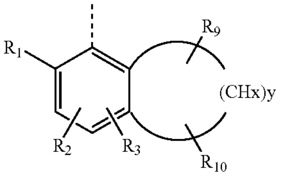

$R_1$ and $R_5$ independently of each other denote hydrogen; $C_1$-$C_{18}$-alkyl; or $C_1$-$C_{12}$-aryl;

$R_2$, $R_3$ and $R_4$ independently of each other denote hydrogen; or a radical of the formula (TBT-01c)

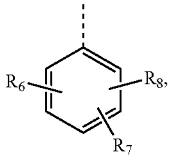

wherein in formula (TBT-01a) at least one of the radicals $R_2$, $R_3$ and $R_4$ denotes a radical of the formula (TBT-01c);

$R_6$, $R_7$, $R_8$, $R_9$ and $R_{10}$ independently of each other denote hydrogen; hydroxyl; halogen; $C_1$-$C_{18}$-alkyl; $C_1$-$C_{18}$-alkoxy; $C_6$-$C_{12}$-aryl; biphenylyl; $C_6$-$C_{12}$-aryloxy; $C_1$-$C_{18}$-alkylthio; carboxyl; —COOM; $C_1$-$C_{18}$-alkylcarboxyl; aminocarbonyl; or mono- or di-$C_1$-$C_{18}$-alkylamino; $C_1$-$C_{10}$-acylamino; —COOH;

M denotes an alkali metal ion;

x denotes 1 or 2; and y denotes an integer from 2 to 10.

Preferably, the UV filters ($d_{17}$) which can be used according to the invention correspond to the compounds of the formula (TBT-02)

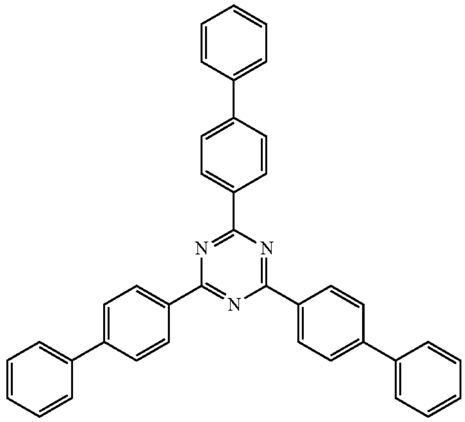

and (TBT-03)

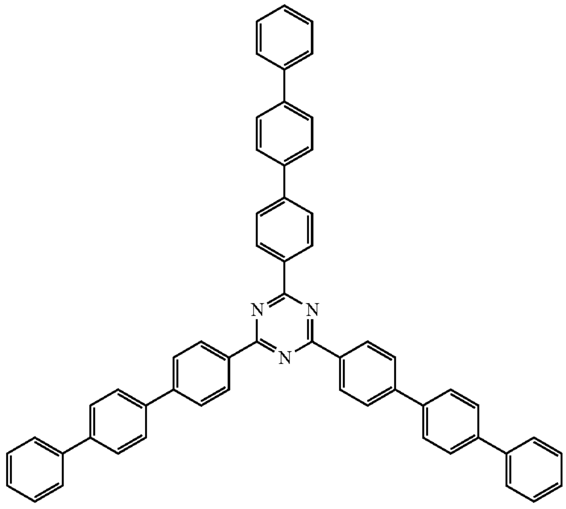

Preferred benzylidenemalonates ($d_{19}$) which can be employed according to the invention correspond to the formula (MBM-01)

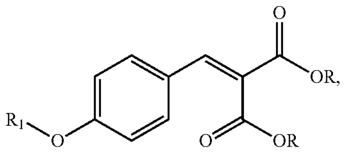

wherein $R_1$ denotes methyl; ethyl; propyl; or n-butyl if $R_1$ denotes methyl, R denotes tert butyl;

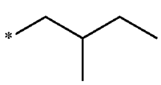

;

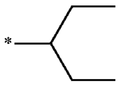

;

a radical of the formula (MBM-01a)

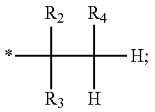

or a radical of the formula (MBM-01b)

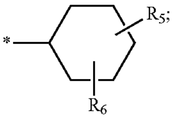

wherein $R_2$ and $R_3$ independently of each other hydrogen; or methyl;

$R_4$ methyl; ethyl; or n-propyl;

$R_5$ and $R_6$ independently of each other hydrogen; or $C_1$-$C_3$-alkyl;

if $R_1$ denotes ethyl; propyl; or n-butyl,

R denotes isopropyl.

Particularly preferred benzylidenemalonates ($d_{19}$) which can be employed according to the invention are listed in the following table:

Examples of benzylidenemalonates which can be used according to the invention

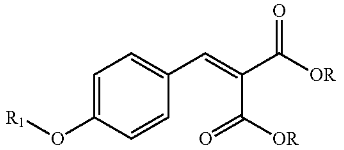

| | $R_1$ | R |
|---|---|---|
| (MBM-02) | methyl | 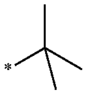 [SMILES: *C(C)(C)C] |
| (MBM-03) | methyl | 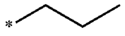 |
| (MBM-04) | methyl | 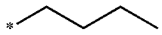 |
| (MBM-05) | methyl | 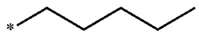 [SMILES: *CCCCC] |
| (MBM-06) | methyl | 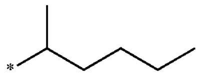 [SMILES: *C(C)CCCC] |
| (MBM-07) | methyl | 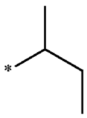 |
| (MBM-08) | methyl | 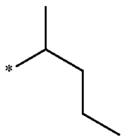 [SMILES: *C(C)CCC] |

-continued

Examples of benzylidenemalonates which can be used according to the invention

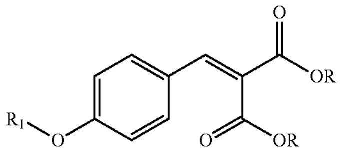

| | $R_1$ | R |
|---|---|---|
| (MBM-09) | methyl | 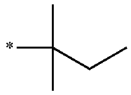 [SMILES: *C(C)(C)CC] |
| (MBM-10) | methyl | 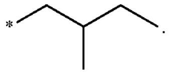 |
| (MBM-11) | ethyl | 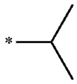 |
| (MBM-12) | propyl | 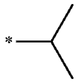 |
| (MBM-13) | n-butyl | 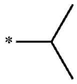 |
| (MBM-14) | methyl | 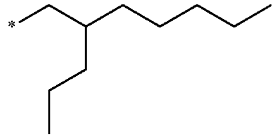 [SMILES: *CC(CCC)CCCCC] |
| (MBM-15) | methyl | 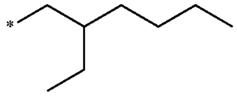 [SMILES: *CC(CC)CCCC] |

An example of a representative of phenylene-bis-diphenyltriazines ($d_{21}$) is 5,6,5,6-tetraphenyl-3,3'-(1,4-phenylene)-bis[1,2,4]triazine corresponds to the formula (PBT-01)

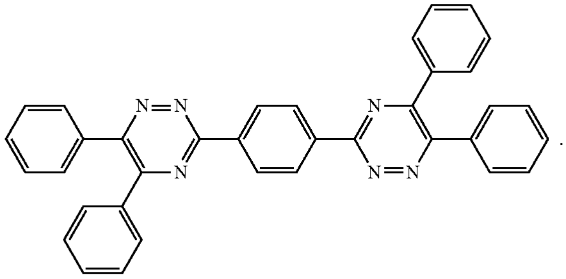

An example of a representative of imidazoline derivatives is Ethylhexyldimethoxybenzyl-idenedioxoimidazoline Propionate An example of a representative of diarylbutadiene derivatives ($d_{23}$) is 1,1-dicarboxy-(2,2'-di-methylpropyl)-4,4-diphenylbutadiene.

Each of the abovementioned UV filters ($d_1$)-($d_{23}$) can be used according to the invention as a mixture. For example, mixtures of two, three, four, five or six of the filter groups ($d_1$)-($d_{23}$) can be used according to the invention. Mixtures of two, three, four, five or six UV filters from one or more representatives of substance classes ($d_1$)-($d_{23}$) can also be used according to the invention.

In a preferred embodiment, the UV filters (d) are representatives of the following compound classes:

($d_1$) p-aminobenzoic acid derivatives;
($d_2$) salicylic acid derivatives;
($d_3$) benzophenone derivatives;
($d_4$) dibenzoylmethane derivatives;
($d_5$) diphenyl acrylates;
($d_6$) 3-imidazol-4-yl-acrylic acid and its esters;
($d_7$) benzofuran derivatives;
($d_9$) cinnamic acid derivatives;
($d_{10}$) camphor derivatives;
($d_{11}$) hydroxyphenyltriazine derivatives;
($d_{12}$) benzotriazole derivatives;
($d_{13}$) trianilino-s-triazine derivatives;
($d_{15}$). menthyl o-aminobenzoates;
($d_{16}$) homosalates;
($d_{19}$) benzylidenemalonates; and
($d_{20}$) merocyanine derivatives.

In a more preferred embodiment, the following oil-soluble UV filters are used according to the invention:

($d_{SOL-1}$) Benzophenone-3 (BP3);
($d_{SOL-2}$) Benzophenone-4 (BP4);
($d_{SOL-3}$) 3-Benzylidene Camphor (3BC);
($d_{SOL-4}$) Bis-Ethylhexyloxyphenol Methoxyphenyl Triazine (BEMT);
($d_{SOL-5}$) Butyl Methoxydibenzoylmethane (BMBM);
($d_{SOL-6}$) Diethylhexyl Butamido Triazone (DBT);
($d_{SOL-7}$) Drometrizole Trisiloxane (DTS);
($d_{SOL-8}$) Ethylhexyl Triazone (EHT);
($d_{SOL-9}$) Ethylhexyl Methoxycinnamate;
($d_{SOL-10}$) Benzylidenemalonate (BM);
($d_{SOL-11}$) Diethylamino Hydroxy Benzoyl Hexyl Benzoate (DHHB);
($d_{SOL-12}$) Octocrylene;
($d_{SOL-13}$) Polysilicone-15;
($d_{SOL-14}$) Homosalate; and
($d_{SOL-15}$) Ethlyhexyl salicylate.

In a most preferred embodiment, the UV filter is at least one selected from the group consisting of ($d_{9a}$) Ethylhexyl Methoxycinnamate,
($d_{11a}$) Bis-Ethylhexyloxyphenol Methoxyphenyl Triazine,
($d_{13a}$) Ethylhexyl Triazone and
($d_{3a}$) Diethylamino Hydroxy Benzoyl Hexyl Benzoate.

In a particularly preferred embodiment, the UV filter is a mixture of UV filters selected from the group consisting of ($d_{9a}$), ($d_{11a}$), ($d_{13a}$) and ($d_{3a}$).

It has been observed that the increase in the absorbance due to the presence of porous metal oxide spheres (e.g., microspheres) is stronger in the UV spectral range compared to the visible range.

In a preferred embodiment, the method further minimizes or masks the whitening effect of the sunscreen composition and maintains its transparency.

In a preferred embodiment, the use further minimizes or masks the whitening effect of the sunscreen composition and maintains its transparency.

The whitening effect of a sunscreen composition is determined by test based on the assessment of light transmittance through a thin film of sunscreen sample spread on roughened substrate.

Sunscreen Composition

In yet another aspect, the presently claimed invention provides a sunscreen composition, comprising water and porous spheres (e.g., microspheres) comprising a metal oxide in the range of 1.0 to 10.0 weight-%, based on total weight of the sunscreen composition, wherein the metal oxide is at least one selected from the group consisting of silica, titania, alumina, zirconia, ceria, iron oxides, zinc oxide, indium oxide, tin oxide and chromium oxide.

In certain embodiments, the metal oxide is at least one selected from the group consisting of silica, zinc oxide and titania. In another embodiment, the metal oxide is silica. In yet another embodiment, the metal oxide is titania.

In certain embodiments, the porous silica spheres have a refractive index in the range from 1.4 to 1.5. When the porous silica spheres are incorporated in a sunscreen composition having refractive index in the same range, e.g. from 1.3 to 1.6, the porous silica spheres do not affect the appearance of the sunscreen composition.

In certain embodiments, the amount of the metal oxide in the porous spheres is in the range of 60.0 to 99.9 weight-%, or in the range of 75.0 to 98.0 weight-% or in the range of 80.0 to 95.0 weight-%, based on total weight of the porous spheres.

In certain embodiments, the sunscreen composition comprises porous spheres having an average diameter in the range of 0.5 μm to 100.0 μm; or 1.0 μm to 90.0 μm; or in the range of 5.0 μm to 80.0 μm; or in the range of 10.0 μm to 70.0 μm; or in the range of 20.0 μm to 50.0 μm.

In certain embodiments, the porous spheres have an average porosity in the range of 0.10 to 0.90.

In certain embodiments, the sunscreen composition comprises porous spheres having an average porosity in the range of 0.10 to 0.80, or in the range of 0.30 to 0.80; or in the range of 0.15 to 0.75; or in the range of 0.25 to 0.60; or in the range of 0.30 to 0.50.

In certain embodiments, the sunscreen composition comprises porous spheres have an average pore diameter in the range of 50 nm to 999 nm; or in the range of 100 nm to 900 nm; or in the range of 200 nm to 800 nm; or in the range of 300 nm to 700 nm; or in the range of 400 nm to 600 nm.

In certain embodiments, the porous spheres are monodisperse.

In certain embodiments, the porous spheres a. have an average diameter in the range of 0.5 μm to 100.0 μm;
b. have an average porosity in the range of 0.10 to 0.90;
c. have an average pore diameter in the range of 50 nm to 999 nm and
d. are monodisperse.

In certain embodiments, the sunscreen composition comprises porous spheres a. have an average diameter in the range of 0.5 μm to 100.0 μm;
b. have an average porosity in the range of 0.10 to 0.80;
c. have an average pore diameter in the range of 50 nm to 999 nm; and
d. are monodisperse.

In certain embodiments, the sunscreen composition further comprises an UV absorber selected from the group consisting of ($d_1$) p-aminobenzoic acid derivatives;
($d_2$) salicylic acid derivatives;

($d_3$) benzophenone derivatives;
($d_4$) dibenzoylmethane derivatives;
($d_5$) diphenyl acrylates;
($d_6$) 3-imidazol-4-yl-acrylic acid and its esters;
($d_7$) benzofuran derivatives;
($d_8$) polymeric UV absorbers;
($d_9$) cinnamic acid derivatives;
($d_{10}$) camphor derivatives;
($d_{11}$) hydroxyphenyltriazine derivatives;
($d_{12}$) benzotriazole derivatives;
($d_{13}$) trianilino-s-triazine derivatives;
($d_{14}$) 2-phenylbenzimidazole-5-sulfonic acid and salts thereof;
($d_{15}$) menthyl o-aminobenzoates;
($d_{16}$) homosalates;
($d_{17}$) tris-biphenyltriazine derivatives;
($d_{18}$) $TiO_2$ (partly encapsulated), ZnO and mica;
($d_{19}$) benzylidenemalonates;
($d_{20}$) merocyanine derivatives;
($d_{21}$) phenylene bis diphenyltriazines;
($d_{22}$) imidazoline derivatives; and
($d_{23}$) diarylbutadiene derivatives.

Representative examples of the UV absorbers are described hereinabove.

In certain embodiments, the sunscreen composition further comprises a dye selected from the group consisting of acid violet 43 and acid red 33.

1) Oil Phase

In certain embodiments, the sunscreen composition further comprises a discontinuous oil phase in the range of 5.0 to 50.0 weight-%, based on total weight of the sunscreen composition.

In the context of the present invention, possible oily substances are, for example, Guerbet alcohols based on fatty alcohols having 6 to 18, preferably 8 to 10 carbon atoms (e.g. Eutanol® G), esters of linear $C_6$-$C_{22}$-fatty acids with linear or branched $C_6$-$C_{22}$-fatty alcohols and esters of branched $C_6$-$C_{13}$-carboxylic acids with linear or branched $C_6$-$C_{22}$-fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In addition, esters of linear $C_6$-$C_{22}$-fatty acids with branched alcohols, in particular 2-ethyl hexanol, esters of $C_3$-$C_{38}$-alkylhydroxycarboxylic acids with linear or branched $C_6$-$C_{22}$-fatty alcohols, in particular diethylhexyl malate, esters of linear and/or branched fatty acids with polyhydric alcohols (such as e.g. propylene glycol, dimer diol or trimer triol) and/or Guerbet alcohols, triglycerides based on $C_6$-$C_{10}$-fatty acids, liquid mono/di/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, plant oils, branched primary alcohols, substituted cyclohexanes, linear and branched $C_6$-$C_{22}$-fatty alcohol carbonates, such as e.g. Dicaprylyl Carbonate (Cetio® GE), Guerbet carbonates based on fatty alcohols having 6 to 18 preferably 8 to 10 C atoms, esters of benzoic acid with linear and/or branched $C_6$-$C_{22}$-alcohols (e.g. Finsolv® TN), linear or branched, symmetric or unsymmetric dialkyl ethers having 6 to 22 carbon atoms per alkyl group, such as e.g. Dicaprylyl Ether (Cetiol® GE), ring-opening products of epoxidized fatty acid esters with polyols (Hydagen® HSP, Sovermol® 750, Sovermol® 1102), silicone oils (cyclomethicone, silicon methicone types and others) and/or aliphatic or naphthenic hydrocarbons, such as e.g. mineral oil, Vaseline, petrolatum, squalene, squalene, iso-hexadecane or dialkylcyclohexanes are suitable in consideration.

In certain embodiments, the oily substances are medium-polarity oils, in particular esters of $C_2$-$C_{12}$-dicarboxylic acids with linear or branched alcohols having 1 to 22 carbon atoms and/or linear and branched $C_6$-$C_{22}$-fatty alcohol carbonates, Adipic acid esters of linear or branched alcohols having 1 to 22 carbon atoms, very particularly of linear alcohols having 1 to 6 carbon atoms, are particularly suitable here.

Linear and branched fatty alcohol carbonates, in particular Dicaprylyl Carbonate, are particularly preferably used as oily substance.

In a more preferred embodiment, dibutyl adipate is used as oily substance.

In another embodiment, the amount of oil phase is in the range of 20 to 35 weight-%, based on total weight of the sunscreen composition.

2) Emulsifier

In certain embodiments, the sunscreen composition further comprises at least one emulsifier in the range of 1.0 to 20.0 weight-%, based on total weight of the sunscreen composition. In certain embodiments, the emulsifier is selected from the group consisting of an anionic emulsifier, a nonionic emulsifier and a polymeric emulsifier.

The anionic surfactants are characterized by one or more anionic group which confers solubility in water, such as e.g. a carboxylate, sulfate, sulfonate or phosphate group, and a lipophilic radical. In addition the molecule can contain polyglycol ether, ester, ether and hydroxyl groups. Anionic surfactants which are tolerated by skin are known to the person skilled in the art in large numbers from relevant handbooks and are commercially obtainable.

Representative examples of the preferred anionic surfactants are, in each case in the form of their salts, ether-carboxylic acids, acylsarcosides having 8 to 24 C atoms in the acyl group, acyltaurides having 8 to 24 C atoms in the acyl group, acylisethionates having 8 to 24 C atoms in the acyl group, sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups, linear alkanesulfonates having 8 to 24 C atoms, linear alpha-olefinsulfonates having 8 to 24 C atoms, alpha-sulfo-fatty acid methyl esters of fatty acids having 8 to 30 C atoms, alkyl sulfates, alkyl polyglycol ether sulfates, esters of tartaric acid and citric acid, alkyl and/or alkenyl ether phosphates, sulfated fatty acid alkylene glycol esters, monoglyceride sulfates and monoglyceride ether sulfates as well as condensation products of $C_8$-$C_{30}$-fatty alcohols with protein hydrolysates and/or amino acids and derivatives thereof, so-called protein fatty acid condensates, e.g. Lamepon®, Guadin®, Hostapon® KCG or Amisoft®.

The salts of these surfactants are preferably selected from the sodium, potassium and ammonium and the mono-, di- and trialkanalammonium salts having 2 to 4 C atoms in the alkanol group.

Particularly suitable anionic surfactants are liquid at room temperature, preferably from 18 to 25° C. A desirable feature in particular of these anionic surfactants is that they have a low water content of at most 10 wt. %, preferably 0.1 to 5 weight-%, based on the total weight of the anionic surfactant.

In a most preferred embodiment, the anionic surfactants are alk(en)yl polyglycol ether citrates and in particular mixtures of mono-, di- and triesters of citric acid and alkoxylated alcohols which correspond to the formula (I):

(I)

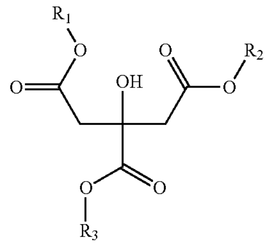

wherein $R_1$, $R_2$ and $R_3$ independently of each other denote hydrogen or the radical of the formula (II) $R_4(OCH_2CHR_5)_n$ wherein $R_4$ represents a linear or branched alkyl and/or alkenyl radical having 6 to 22 carbon atoms, $R_5$ represents hydrogen or a methyl radical and n represents a number from 1 to 20, with the condition that at least one of the radicals $R_1$, $R_2$ or $R_3$ is other than hydrogen.

Typical examples of the alcohol part of the esters are addition products of on average 1 to 20 mol, preferably 5 to 10 mol of ethylene oxide and/or propylene oxide on caproyl alcohol, capryl alcohol, 2-ethylhexyl alcohol, capric alcohol, lauryl alcohol, isotridecyl alcohol, myristyl alcohol, cetyl alcohol, palmitolelyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical grade mixtures thereof.

Such alk(en)yl polyglycol ether citrates are advantageous for the agents according to the invention since they are liquid anionic surfactants having a low water content of max. 5 wt. %, based on the anionic surfactant.

The anionic surfactants are preferably present in amounts in the range of 7 to 17 weight-%, based on total weight of the sunscreen composition.

The agents according to the invention furthermore comprise at least (c) 0.5 to 25 wt. % of a further co-surfactant which differs from anionic surfactants.

Suitable co-surfactants are, in principle, zwitterionic, ampholytic, cationic and/or nonionic surfactants.

Those surface-active compounds which carry at least one quaternary ammonium group and at least one —COO(—) or —$SO_3$(—) group in the molecule are called zwitter-ionic surfactants. Particularly suitable zwitter-ionic surfactants are the so-called betaines, such as the N-alkyl-N,N-dimethylammonium glycinates, for example coco-alkyldimethylammonium glycinate, N-acylaminopropyl-N,N-dimethylammonium glycinates, for example coco-acylamimopropyldimethylammonium glycinate, and 2-alkyl-3-carboxymethyl-3-hydroxyethylimidazoline having in each case 8 to 18 C atoms in the alkyl or acyl group, and coco-acylaminoethylhydroxy-ethylcarboxymethyl glycinate. The fatty acid amide derivative known under the INCI name Cocamidopropyl Betaine is a preferred zwitter-ionic surfactant. Tego® Betain 810 (INCI: Capryl/Capramidopropyl Betaine) and a surfactant mixture of Rewopol® SBCS 50K (INCI: Disodium PEG-5 Laurylcitrate Sulfosuccinate, Sodium Laureth Sulfate) and Tego® Betain 810 (Capryl/Capramidopropyl Betaine), in particular in the weight ratio of 1:4 to 4:1, very particularly preferably in the weight ratio of from 1:4 to 1:1, are particularly preferred according to the invention.

Ampholytic surfactants are understood as meaning those surface-active compounds which contain, apart from a $C_8$-$C_{18}$-alkyl or acyl group, at least one free amino group and at least one —COOH or —$SO_3H$ group in the molecule and are capable of formation of inner salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 C atoms in the alkyl group. Preferred ampholytic surfactants are N-coco-alkylaminopropionate, coco-acylaminoethylaminopropionate and $C_{12}$-$C_{18}$ acylsarcosine.

Quaternary ammonium compounds in particular can be used as cationic surfactants. Surfactants from this substance class have a particularly high affinity for the skin and can improve the degree of sensory smoothness. These include, inter alfa, ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. The very readily biodegradable quaternary ester compounds, such as, for example, the dialkylammonium methosulfates and methylhydroxyalkyldialkoyloxyalkylammonium methosulfates marketed under the trade name Stepantex® and the corresponding products of the Dehyquart® series, can furthermore be employed as cationic surfactants. The term "esterquats" is in general understood as meaning quaternized fatty acid triethanolamine ester salts. They impart to the compositions particularly soft feel. These are known substances which are prepared by the relevant methods of organic chemistry. Further cationic surfactants which can be used according to the invention are the quaternized protein hydrolysates.

Nonionic surfactants are particularly preferably present as co-surfactants, for example

- addition products of from 2 to 50 mol of ethylene oxide and/or 0 to 20 mol of propylene oxide on linear fatty alcohols having 8 to 40 C atoms, on fatty acids having 12 to 40 C atoms and on alkylphenols having 8 to 15 C atoms in the alkyl group;
- $C_{12/18}$ fatty acid mono- and diesters of addition products of from 1 to 50 mol of ethylene oxide on glycerol; glycerol mono- and diesters and sorbitan mono- and diesters of saturated and unsaturated fatty acids having 6 to 22 carbon atoms and ethylene oxide addition products thereof, alkyl mono- and oligoglycoside having 8 to 22 carbon atoms in the alkyl radical and ethoxylated analogues thereof; addition products of from 7 to 60 mol of ethylene oxide on castor oil and/or hydrogenated castor oil;

polyol and/or polyglycerol esters, such as e.g. polyglycerol diisostearate or polyglycerol dimerate or polyglycerol 12-hydroxystearate;

addition products of from 2 to 15 mol of ethylene oxide on castor oil and/or hydrogenated castor oil;

partial esters based on linear, branched, unsaturated or saturated $C_6$-$C_{22}$-fatty acids, ricinoleic acid and 12-hydroxystearic acid with, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose), or mixed esters, such as e.g. glyceryl stearate citrate and glyceryl stearate lactate;

wool wax alcohols;

polysiloxane/polyalkyl polyether copolymers and corresponding derivatives;

mixed esters of pentaerythritol, fatty acids, citric acid and fatty alcohol and/or mixed esters of fatty acids having 6 to 22 carbon atoms, methylglucose and polyols, preferably glycerol or polyglycerol; and polyalkylene glycols.

The addition products of ethylene oxide and/or of propylene oxide on fatty alcohols, fatty acids, alkylphenols, glycerol mono- and diesters and sorbitan mono- and diesters of fatty acids or on castor oil are known, commercially obtainable products. These are homologue mixtures, the average degree of alkoxylation of which corresponds to the ratio of the substance amounts of ethylene oxide and/or propylene oxide and substrate with which the addition reaction is carried out. They are W/O or O/W emulsifiers, depending on the degree of ethoxylation. For the preparations according to the invention, the reaction products with 1-100 mol of ethylene oxide are particularly suitable.

Advantageous compounds from the group of nonionic surfactants are partial esters of polyols, in particular of $C_3$-$C_6$-polyols, such as, for example, glyceryl monoesters, partial esters of pentaerythritol or sugar esters, e.g. sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan tri hydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical grade mixtures thereof. Addition products of from 1 to 30, preferably 5 to 10 mol of ethylene oxide on the sorbitan esters mentioned are also suitable nonionic surfactants.

Nonionic surfactants from the group of alkyl oligoglycosides are particularly skin-friendly and may therefore preferably be suitable in the context of the invention. $C_8$-$C_{22}$-alkyl mono- and oligoglycosides, their preparation and their use are known from the prior art. Their preparation is carried out in particular by reaction of glucose or oligosaccharides with primary alcohols having 8 to 22 C atoms, preferably 12 to 22, and particularly preferably 12 to 18 C atoms. With respect to the glycoside radical, both monoglycosides in which a cyclic sugar residue is bonded glycosidically to the fatty alcohol and oligomeric glycosides having a degree of oligomerization of up to preferably about 8 are suitable. The degree of oligomerization here is a statistical mean based on a conventional distribution of homologues for such technical grade products Products which are available under the name Plantacare® contain a glucosidically bonded $C_8$-$C_{16}$-alkyl group on an oligoglucoside radical, the average degree of oligomerization of which is 1 to 2. The acylglucamides derived from glucamine are also suitable as nonionic surfactants.

Nonionic surfactants, preferably polyol and/or polyglycerol esters, are very particularly preferably present as co-surfactants in the agents according to the invention as component (c), and/or alkyl oligoglycosides.

The polyol component of these surfactants can be derived from substances which have at least two, preferably 3 to 12 and in particular 3 to 8 hydroxyl groups and 2 to 12 carbon atoms.

Typical examples are:

glycerol and polyglycerol;

alkylene glycols, such as, for example, ethylene glycol, diethylene glycol, propylene glycol;

methylol compounds, such as, in particular, trimethylolethane, trimethylolpropane, trimethylolbutane, pentaerythritol and dipentaerythritol;

alkyl oligoglucosides having 1 to 22, preferably 1 to 8 and in particular 1 to 4 carbons in the alkyl radical, such as, for example, methyl and butyl glucoside;

sugar alcohols having 5 to 12 carbon atoms, such as, for example, sorbitol or mannitol;

sugars having 5 to 12 carbon atoms, such as, for example, glucose or sucrose;

amino-sugars, such as, for example, glucamine.

Reaction products based on polyglycerol are of particular importance because of their excellent use properties.

The acid component of these surfactants can be derived from straight-chain, branched, saturated and/or unsaturated carboxylic acids, optionally with functional groups, such as hydroxyl groups. The acid component is particularly preferably fatty acids having 12 to 22 carbon atoms, which optionally carry a hydroxyl group, and in particular hydroxystearic acid.

In a preferred embodiment of the invention the diester of polyhydroxystearic acid, polyglyceryl 2-dipolyhydroxystearate, which is marketed, for example, by BASF Personal Care and Nutrition GmbH under the name Dehymuls® PGPH, is used as a glyceryl ester.

In the agents according to the invention the further co-surfactants are conventionally present in an amount in the range of 0.5 to 25 weight-%; more preferably in the range of 3.0 to 18 weight-%; and particularly preferably in the range of 7 to 18 weight-%.

3) Additives

In certain embodiments, the sunscreen composition further comprises additives selected from the group consisting of thickener, active ingredients, preservatives and perfumes.

Thickeners

Suitable thickeners are anionic, zwitterionic, amphoteric and nonionic copolymers, such as, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, acrylamidopropyltrimethylammonium chloride/acrylate copolymers, octylacrylamide/methyl methacrylate/tert-butylaminoethyl methacrylate/2-hydroxypropyl methacrylate polymers, vinylpyrrolidone/ vinyl acetate copolymers, vinylpyrrolidone/dimethylaminoethyl methacrylate/vinylcaprolactam terpolymers and optionally polysaccharides, in particular xanthan gum, guar and guar derivatives, agar-agar, alginates and tyloses, cellulose and cellulose derivatives, such as carboxymethylcellulose, carboxymethylcellulose and hydroxycellulose and moreover silicones.

Preferably, thickeners selected from the group of polyacrylates and crosslinked polyacrylates, such as Rheocare TTA®, Cosmedia® SP, Rheocare® C Plus, Tinovis® ADE, Tinovis® GTC, are added.

Thickeners from the group of polysaccharides, such as Ketro® T or Rheocare® XG, are furthermore preferred.

Preferably, the amounts of thickener is in the range from 0.5 to 5 weight-%, in particular from 1. to 4 weight-%, calculated as active substance and based on total weight of the sunscreen composition.

The thickeners can be added to the concentrated agent before the dilution with water is carried out or can be contained in the water with which the dilution of the concentrated agent is carried out.

According to a preferred process variant, the concentrated agent is mixed with the thickener, and water for dilution is added to this mixture and the further formulation constituents are optionally stirred in.

According to another preferred process variant, the water, the thickener and optionally the other auxiliary substances are stirred with one another and the concentrated agent is added to this mixture.

The sunscreen final formulations prepared by the process according to the invention are often particularly finely divided 0/W emulsion having an average particle size of <10 μm, preferably <5 μm.

Active Compounds

Biogenic active compounds which are suitable according to the invention are to be understood as meaning, for example, tocopherol, tocopherol acetate, tocopherol palmitate, ascorbic acid, (deoxy)ribonucleic acid and fragmentation products thereof, 0-glucans, retinol, bisabolol, allantoin, phytantriol, panthenol, AHA acids, amino acids, ceramides, pseudoceramides, essential oils, plant extracts, such as e.g. Prunus extract, Bambara nut extract and vitamin complexes. Such active compounds are employed in sunscreen final formulations as agents which trap free radicals, and serve to regenerate the skin.

Preservatives

Suitable preservatives are, for example, phenoxyethanol, formaldehyde solution, parabens, pentanediol or sorbic acid and the silver complexes known by the name Surfacine®.

Perfume Oils

Perfume oils which may be mentioned are natural, plant and animal as well as synthetic odoriferous substances or mixtures thereof. Natural odoriferous substances are obtained, inter alfa, by extraction of flowers, stems, leaves, fruit, fruit peel, roots and resins of plants. Animal raw materials are furthermore possible, such as, for example, civet and castoreum. Typical synthetic odoriferous compounds are products of the ester, ether, aldehyde, ketone, alcohol and hydrocarbon type. Preferably, mixtures of various odoriferous substances which together generate a pleasant fragrance note are used.

Auxiliary Substances

In certain embodiments, the sunscreen final formulations further comprise auxiliary substances, such as moisture-retaining agents/skin-moisturizing agents, viscosity regulators, oils, fats and waxes, surfactants, pearlescent waxes, super-oiling agents, stabilizers, cationic, zwitterionic or amphoteric polymers, further UV filters, biogenic active compounds, film-forming agents, swelling agents, hydrotropic substances, preservatives, solubilizers, perfume oils, dyestuffs, insect repellant active compounds etc., which are listed below by way of example.

Moisture-retaining agents serve to further optimize the sensory properties of the composition and for moisture regulation of the skin. The moisture-retaining agents can be present in an amount in the range of 0 to 5.0 weight-%, based on total weight of the sunscreen composition.

Suitable substances are, inter alfa, amino acids, pyrrolidonecarboxylic acid, lactic acid and salts thereof, lactitol, urea and urea derivative, uric acid, glucosamine, creatinine, collagen cleavage products, chitosan or chitosan salts/derivatives, and in particular polyols and polyol derivatives (e.g. glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sucrose, sorbitylsilanediol, sucrose, trehalose, xylose, xylitol, glucuronic acid and salts thereof), ethoxylated sorbitol (sorbeth-6, sorbeth-20, sorbeth-30, sorbeth-40), honey and hardened honey, hardened starch hydrolysates and mixtures of hardened wheat protein and PEG-20/acetate copolymer. Substances which are preferably suitable according to the invention as moisture-retaining agents are glycerol, diglycerol, triglycerol and butylene glycol.

Possible insect repellants are, for example, N,N-diethyl-m-toluamide, 1,2-pentanediol or 3-(N-n-butyl-N-acetylamino)propionic acid ethyl ester), which is marketed by Merck KGaA under the name Insect Repellent 3535, and butylacetylaminoproprionate. They are conventionally employed in the compositions according to the invention in an amount in the range of 0 to 6 weight-%, based on total weight of the sunscreen composition.

The viscosity of the agents according to the invention can be achieved by addition of viscosity regulators. Possible viscosity regulators are, inter alfa, agents which impart consistency, such as e.g. fatty alcohols or hydroxy-fatty alcohols having 12 to 22 and preferably 16 to 18 carbon atoms and partial glycerides, fatty acids having 12 to 22 carbon atoms or 12-hydroxy-fatty acids. A combination of these substances with alkyl oligoglucosides and/or fatty acid N-methylglucamides of the same chain length is also suitable, since such combinations deliver particularly stable and homogeneous emulsions. The viscosity regulators also include thickening agents, such as, for example, Aerosil types (hydrophilic silicic acids), polysaccharides, in particular xanthan gum, guar-guar, agar-agar, alginates and tyloses, carboxymethylcellulose and hydroxyethyl- and hydroxypropylcellulose, furthermore higher molecular weight polyethylene glycol mono- and diesters of fatty acids, polyacrylates (e.g. Carbopols® and Pemulen types from Goodrich; Synthalens® from Sigma; Keltrol types from Kelco; Sepigel types from Seppic; Salcare types from Allied Colloids), non-crosslinked and polyol-crosslinked polyacrylic acids, polyacrylamides, polyvinyl alcohol and polyvinylpyrrolidone. Bentonites, such as e.g. Bentone® Gel VS-5PC (Rheox), which is a mixture of cyclopentasiloxane, Disteardimonium Hectorite and propylene carbonate, have also proved to be particularly effective. Surfactants, such as, for example, ethoxylated fatty acid glycerides, esters of fatty acids with polyols, such as, for example, pentaerythritol or trimethylolpropane, fatty alcohol ethoxylates with a narrowed homologue distribution, alkyl oligoglucosides and electrolytes, such as e.g. sodium chloride and ammonium chloride, can also be employed for regulation of the viscosity.

In the context of the invention fats and waxes are understood as meaning all lipids having a fat- or wax-like consistency which have a melting point above 20° C. These include, for example, the classic triacylglycerols, that is to say the triesters of fatty acids with glycerol, which can be of plant or animal origin. These can also be mixed esters, that is to say triesters of glycerol with various fatty acids, or a mixture of various glycerides. These also include mixtures of mono-, di- and triglycerides. So-called hardened fats and oils which are obtained by partial hydrogenation are particularly suitable according to the invention. Hardened fats and oils of plants are preferred, e.g. hydrogenated castor oil, groundnut oil, soya oil, rape oil, beet seed oil, cottonseed oil, soya oil, sunflower oil, palm oil, palm kernel oil, linseed oil, almond oil, maize oil, olive oil, sesame oil, cacao butter and coconut fat. Oxidation-stable plant glycerides which are available under the name Cegesoft® or Novata® are particularly suitable.

Possible waxes are, inter alfa, natural waxes, such as e.g. candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygium fat, ceresin, ozocerite (earth wax), petrolatum, paraffin waxes, microwaxes; chemically modified waxes (hard waxes), such as e.g. montan ester waxes, Sasol waxes, hydrogenated jojoba waxes and synthetic waxes, such as e.g. polyalkylene waxes and polyethylene glycol waxes.

In addition to the fats, fat-like substances, such as lecithins and phospholipids, are also possible as additives. Lecithins are glycero-phospholipids which are formed from fatty acids, glycerol, phosphoric acid choline by esterification, and are often also called phosphatidylcholines (PC). Cephalins, which are also called phosphatidic acids and are derivatives of 1,2-diacyl-sn-glycerol-3-phosphoric acids, may be mentioned as an example of natural lecithins. In contrast, phospholipids are usually understood as meaning mono- and preferably diesters of phosphoric acid with glycerol (glycerol phosphates). Sphingosines and sphingolipids are also possible as fat-like substances.

Suitable pearlescent waxes are, for example, alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with $C_6$-$C_{22}$-fatty alcohols, specifically long-chain esters of tartaric acid; fatty substances, such as, for example, fatty alcohols, fatty ketones, fatty alde-hydes, fatty ethers and fatty carbonates, which have at least 24 carbon atoms in total—specifically Lauron®; distearyl ether; fatty acids, such as stearic acid, $C_{12}$-$C_{22}$-hydroxy-fatty acids, behenic acid, ring-opening products of $C_{12}$-$C_{22}$-olefin epoxides with $C_{12}$-$C_{22}$-fatty alcohols and/or polyols having 2 to 15 carbon atoms and 2 to 10 hydroxyl groups and mixtures thereof.

Super-oiling agents which can be used are substances such as, for example, lanolin and lecithin and polyethoxylated or acylated derivatives of lanolin and lecithin, polyol fatty acid esters, monoglycerides and fatty acid alkanolamides, the latter simultaneously serving as foam stabilizers.

So-called stabilizers which can be employed are metal salts of fatty acids, such as e.g. magnesium, aluminum and/or zinc stearate or ricinoleate.

Suitable cationic polymers which further optimize the sensory properties of the compositions according to the invention and impart to the skin a sensation of softness are, for example, cationic cellulose derivatives, such as e.g. a quaternized hydroxyethylcellulose which is obtainable from Amerchol under the name Polymer JR 400®, cationic starch, copolymers of di-allylammonium salts and acrylamides, quaternized vinylpyrrolidone/vinylimidazole polymers, such as e.g. Luviquat® (BASF), condensation products of polyglycols and amines, quaternized collagen polypeptides, such as, for example, Lauryldimonium Hydroxypropyl Hydrolyzed Collagen (Lamequat® L/Griinau), quaternized wheat polypeptides, polyethylenimine, cationic silicone polymers, such as e.g. amodimethicone, copolymers of adipic acid and dimethylamino-hydroxypropyldiethylenetriamine (Cartaretine®/Sandoz), copolymers of acrylic acid with di-methyldiallylammonium chloride (Merquat® 550/Chemviron, polyaminopolyamides and crosslinked water-soluble polymers thereof, cationic chitin derivatives, such as, for example, quaternized chitosan, condensation products, optionally distributed in microcrystalline form, of dihaloalkyls, such as e.g. dibromobutane with bisdialkylamines, such as e.g. bis-dimethyl-amino-1,3-propane, cationic guar gum, such as e.g. Jaguar® CBS, Jaguar® C-17, Jaguar® C-16 from Celanese, quaternized ammonium salt polymers, such as e.g. Mirapol® A-15, Mirapol® AD-1, Mirapol® AZ-1 from Miranol.

Starch derivative can furthermore be employed to improve the skin sensation, e.g. Dry Flo® PC (INCI: Aluminum Starch Octenylsuccinate).

Suitable silicone compounds have already been mentioned with the oily substances. In addition to dimethylpolysiloxanes, methylphenylpolysiloxanes and cyclic silicones, amino-, fatty acid-, alcohol-, polyether-, epoxy-, fluorine-, glycoside- and/or alkyl-modified silicone compounds, which can be either liquid or resinous at room temperature, are also suitable. Simethicones, which are mixtures of dimethicones having an average chain length of from 200 to 300 dimethylsiloxane units and silicon dioxide or hydrogenated silicates, are furthermore suitable.

So-called film-forming agents which lead to a further improvement in the sensory properties of the preparations according to the invention are, for example, chitosan, microcrystalline chitosan, quaternized chitosan, collagen, hyaluronic acid and salts thereof and similar compounds, and the polyvinylpyrrolidones, vinylpyrrolidone/vinyl acetate copolymers, polymers of the acrylic acid series and quaternized cellulose derivatives already mentioned under the viscosity regulators.

To improve the flow properties of the compositions according to the invention hydrotropic substances, such as, for example, ethanol, isopropyl alcohol, or polyols, can furthermore be employed. Polyols which are possible here have preferably 2 to 15 carbon atoms and at least two hydroxyl groups. The polyols can also contain further functional groups, in particular amino groups, or can be modified with nitrogen.

Dyestuffs which can be used are the substances which are suitable and approved for cosmetic purposes.

The presently claimed invention offers one or more of the following advantages:

1. The present invention provides a method for increasing sun protection factor of a sunscreen composition using porous spheres comprising metal oxide.
2. The method increases SPF of a sunscreen formulation while minimizing or masking its whitening effect and maintaining its transparency.

3. The porous metal oxide spheres of the present invention can be used for increasing SPF of a sunscreen composition.
4. The porous metal oxide spheres of the present invention are useful for increasing SPF of a sunscreen composition while minimizing or masking its whitening effect and maintaining its transparency.

In the following, there are provided a list of embodiments to further illustrate the present disclosure without intending to limit the disclosure to specific embodiments listed below.

1. A method for increasing the sun protection factor of a sunscreen composition, the method comprising adding porous spheres comprising a metal oxide to the sunscreen composition, wherein the metal oxide is at least one selected from the group consisting of silica, titania, alumina, zirconia, ceria, iron oxides, zinc oxide, indium oxide, tin oxide and chromium oxide.
2. Use of porous spheres comprising a metal oxide for increasing the sun protection factor of a sunscreen composition, wherein the metal oxide is at least one selected from the group consisting of silica, titania, alumina, zirconia, ceria, iron oxides, zinc oxide, indium oxide, tin oxide and chromium oxide.
3. The method or use according to embodiments 1 or 2, wherein the porous spheres are present in an amount in the range of 0.1 to 10.0 weight-%, based on total weight of the sunscreen composition.
4. The method or use according to any of the preceding embodiments, wherein the amount of the metal oxide in the porous spheres is in the range of 60.0 to 99.9 weight-%, based on total weight of the porous spheres.
5. The method or use according to any of the preceding embodiments, wherein the porous spheres have an average diameter in the range of 0.5 μm to 100.0 μm.
6. The method or use according to any of the preceding embodiments, wherein the porous spheres have an average porosity in the range of 0.10 to 0.90.
7. The method or use according to any of the preceding embodiments, wherein the porous spheres have an average porosity in the range of 0.10 to 0.80.
8. The method or use according to any of the preceding embodiments, wherein the porous spheres are monodisperse.
9. The method or use according to any of the preceding embodiments, wherein the porous spheres have an average pore diameter in the range of 50 nm to 999 nm.
10. The method or use according to any of the preceding embodiments, wherein the porous spheres have more than one population of pores each having an average pore diameter, wherein each population has a different average pore diameter.
11. The method or use according to any of the preceding embodiments, wherein the porous spheres
    a. have an average diameter in the range of 0.5 μm to 100.0 μm;
    b. have an average porosity in the range of 0.10 to 0.90;
    c. have an average pore diameter in the range of 50 nm to 999 nm and
    d. are monodisperse.
12. The method or use according to any of the preceding embodiments, wherein the porous spheres
    a. have an average diameter in the range of 0.5 μm to 100.0 μm;
    b. have an average porosity in the range of 0.10 to 0.80;
    c. have an average pore diameter in the range of 50 nm to 999 nm; and
    d. are monodisperse.
13. The method or use according to any of the preceding embodiments, wherein the sunscreen composition further comprises an UV absorber selected from the group consisting of
    ($d_1$) p-aminobenzoic acid derivatives;
    ($d_2$) salicylic acid derivatives;
    ($d_3$) benzophenone derivatives;
    ($d_4$) dibenzoylmethane derivatives;
    ($d_5$) diphenyl acrylates;
    ($d_6$) 3-imidazol-4-yl-acrylic acid and its esters;
    ($d_7$) benzofuran derivatives;
    ($d_8$) polymeric UV absorbers;
    ($d_9$) cinnamic acid derivatives;
    ($d_{10}$) camphor derivatives;
    ($d_{11}$) hydroxyphenyltriazine derivatives;
    ($d_{12}$) benzotriazole derivatives;
    ($d_{13}$) trianilino-s-triazine derivatives;
    ($d_{14}$) 2-phenylbenzimidazole-5-sulfonic acid and salts thereof;
    ($d_{15}$). menthyl o-aminobenzoates;
    ($d_{16}$) homosalates;
    ($d_{17}$) tris-biphenyltriazine derivatives;
    ($d_{18}$) $TiO_2$ (partly encapsulated), ZnO and mica;
    ($d_{19}$) benzylidenemalonates;
    ($d_{20}$) merocyanine derivatives;
    ($d_{21}$) phenylene bis diphenyltriazines;
    ($d_{22}$) imidazoline derivatives; and
    ($d_{23}$) diarylbutadiene derivatives.
14. The method according to any of the preceding embodiments, wherein the method further minimizes or masks the whitening effect of the sunscreen composition and maintains its transparency.
15. The use according to any of the preceding embodiments, wherein the use further minimizes or masks the whitening effect of the sunscreen composition and maintains its transparency.
16. A sunscreen composition comprising water and porous spheres comprising a metal oxide in the range of 1.0 to 10.0 weight-%, based on total weight of the sunscreen composition, wherein the metal oxide is at least one selected from the group consisting of silica, titania, alumina, zirconia, ceria, iron oxides, zinc oxide, indium oxide, tin oxide and chromium oxide.
17. The sunscreen composition according to embodiment 16, further comprising a discontinuous oil phase in the range of 5.0 to 50.0 weight-%, based on total weight of the sunscreen composition.
18. The sunscreen composition according to embodiments 16 or 17, further comprising at least one emulsifier in the range of 1.0 to 20.0 weight-%, based on total weight of the sunscreen composition.
19. The sunscreen composition according to embodiment 18, wherein the emulsifier is selected from the group consisting of an anionic emulsifier, a nonionic emulsifier and a polymeric emulsifier.
20. The sunscreen composition according to any of embodiments 16 to 19, further comprises additives selected from the group consisting of thickener, active ingredients, preservatives and perfumes.
21. The sunscreen composition according to any of embodiments 16 to 20, wherein the amount of the metal oxide in the porous spheres is in the range of 60.0 to 99.9 weight-%, based on total weight of the porous spheres.

22. The sunscreen composition according to any of embodiments 16 to 21, wherein the porous spheres have an average diameter in the range of 0.5 μm to 100.0 μm.
23. The sunscreen composition according to any of embodiments 16 to 22, wherein the porous spheres have an average porosity in the range of 0.10 to 0.90.
24. The sunscreen composition according to any of embodiments 16 to 23, wherein the porous spheres have an average porosity in the range of 0.10 to 0.80.
25. The sunscreen composition according to any of embodiments 16 to 24, wherein the porous spheres have an average pore diameter in the range of 50 nm to 999 nm.
26. The sunscreen composition according to any of embodiments 16 to 25, wherein the porous spheres are monodisperse.
27. The sunscreen composition according to any of embodiments 16 to 26, wherein the porous spheres
    a. have an average diameter in the range of 0.5 μm to 100.0 μm;
    b. have an average porosity in the range of 0.10 to 0.90;
    c. have an average pore diameter in the range of 50 nm to 999 nm and
    d. are monodisperse.
28. The sunscreen composition according to any of embodiments 16 to 27, wherein the porous spheres
    a. have an average diameter in the range of 0.5 μm to 100.0 μm;
    b. have an average porosity in the range of 0.10 to 0.80;
    c. have an average pore diameter in the range of 50 nm to 999 nm; and
    d. are monodisperse.
29. The sunscreen composition according to any of embodiments 16 to 28, wherein the sunscreen composition further comprises an UV absorber selected from the group consisting of
    ($d_1$) p-aminobenzoic acid derivatives;
    ($d_2$) salicylic acid derivatives;
    ($d_3$) benzophenone derivatives;
    ($d_4$) dibenzoylmethane derivatives;
    ($d_5$) diphenyl acrylates;
    ($d_6$) 3-imidazol-4-yl-acrylic acid and its esters;
    ($d_7$) benzofuran derivatives;
    ($d_8$) polymeric UV absorbers;
    ($d_9$) cinnamic acid derivatives;
    ($d_{10}$) camphor derivatives;
    ($d_{11}$) hydroxyphenyltriazine derivatives;
    ($d_{12}$) benzotriazole derivatives;
    ($d_{13}$) trianilino-s-triazine derivatives;
    ($d_{14}$) 2-phenylbenzimidazole-5-sulfonic acid and salts thereof;
    ($d_{15}$). menthyl o-aminobenzoates;
    ($d_{16}$) homosalates;
    ($d_{17}$) tris-biphenyltriazine derivatives;
    ($d_{18}$) $TiO_2$ (partly encapsulated), ZnO and mica;
    ($d_{19}$) benzylidenemalonates;
    ($d_{20}$) merocyanine derivatives;
    ($d_{21}$) phenylene bis diphenyltriazines;
    ($d_{22}$) imidazoline derivatives; and
    ($d_{23}$) diarylbutadiene derivatives.
30. The sunscreen composition according to any of embodiments 16 to 29, wherein the sunscreen composition further comprises a dye selected from the group consisting of acid violet 43 and acid red 33.

Having generally described the invention, a further understanding can be obtained by reference to certain specific examples which are provided herein for the purpose of illustration only, and are not intended to be limiting unless otherwise specified.

EXAMPLES

The presently claimed invention is further illustrated in combination with the following examples. These examples are provided to exemplify the presently claimed invention, but are not intended to restrict the scope of the presently claimed invention in any way.

Materials

Acid Blue 3 (Patent Blue V) is 2-[(4-diethylaminophenyl)(4-diethylimino-2,5-cyclohexadien-1-ylidene)methyl]-4-hydroxy-1,5-benzene-disulfonate, and is available from Sigma Aldrich.

Benzophenone-4 is 2-hydroxy-4-methoxybenzophenone-5-sulfonic acid is available from BASF.

SunsH® 130 is available from Sunjin Beauty Science (formerly Sunjin Chemical)

Sunsphere is available from Dow chemicals.

Methods

Average diameter or particle size: Particle size is synonymous with particle diameter and was determined by scanning electron microscopy (SEM) or transmission electron microscopy (TEM).

Average porosity and average pore diameter: Mercury porosimetry analysis was used to characterize the porosity of the spheres. Mercury porosimetry applies controlled pressure to a sample immersed in mercury. External pressure is applied for the mercury to penetrate into the voids/pores of the material. The amount of pressure required to intrude into the voids/pores is inversely proportional to the size of the voids/pores. The mercury porosimeter generates volume and pore size distributions from the pressure versus intrusion data generated by the instrument using the Washburn equation. For example, porous silica spheres containing voids/pores with an average size of 165 nm have an average porosity of 0.8.

Determination of the In Vitro SPF of Formulation Examples

The determination of the in vitro SPF is performed by measuring the diffuse transmission in the UV-range using a Labsphere Ultraviolet Transmittance Analyzer 2000S. In order to simulate the inhomogeneous surface structure of human skin, substrates with rough or porous surface are taken for such measurements. For this method Sandblasted 4-5 μm PMMA (PolyMethylMethacrylate) plates, from Helioscience (France), are used as substrate.

The sunburn protection factor (SPF) formalism was first introduced by Sayre in 1979 [1], by which an average of the inverse transmission (1/T) of the respective sunscreen in the spectral range between 290 and 400 nm is calculated, including weighting with the irradiance spectrum of a UV source, Ss(λ), and the erythema) action spectrum, Ser(λ):

$$SPF_{nvtro} = \frac{\sum_{290}^{400} s_{er}(\lambda) \cdot S_s(\lambda)}{\sum_{290}^{400} s_{er}(\lambda) \cdot S_s(\lambda) \cdot T(\lambda)}$$

References

[1] R. M. Sayre, P. P. Agin, G. J. LeVee, E. Marlowe. A comparison of in vivo and in vitro testing of sunscreening formulas, Photochem. Photobiol. 29 (1979) 559-566

Transparency/whitening method: Color measurements were performed with the prepared compositions applied on PMMA plates also used for in vitro SPF measurement. From the obtained L*a*b* parameters L* refers to the lightness of a sample. The difference of L* to a blank sample is expressed as delta L* and can be used to compare the transparency or whitening of the samples.

Preparation of Porous Metal Oxide Spheres

Example 1: Porous Silica Spheres

A styrene/acrylic acid copolymer was prepared as follows: 230 mL Deionized (DI) water was added to a 3-neck reaction flask equipped with a thermometer, condenser, magnetic stirring and nitrogen atmosphere. The water was heated to 80° C. and 10 g of styrene was added with stirring, followed by addition of 100 mg acrylic acid dissolved in 10 mL DI water via syringe. 100 mg of ammonium persulfate was dissolved in 10 mL DI water and added to the stirred mixture via syringe. The reaction mixture was stirred for 24 hours at 80° C. The polymer colloid dispersion was allowed to cool to room temperature and was purified via centrifugation, producing polystyrene nanospheres having an average particle size of 250 nm.

The aqueous polystyrene colloid dispersion was diluted to 1 weight-% with deionized water and 1 weight-% silica nanoparticles were added and the mixture was sonicated to prevent particle agglomeration. A continuous oil phase used was 0.1 weight-% polyethylene glycol/perfluoropolyether surfactant in a fluorinated oil. The aqueous colloid dispersion and oil were each injected into a microfluidic device having a 50 μm droplet junction via syringes associated with pumps. The system was allowed to equilibrate until monodisperse droplets were produced. The monodisperse droplets were collected in a reservoir.

Collected droplets were dried in an oven at 45° C. for 4 hours to provide monodisperse polymer template spheres. The polymer template spheres were calcined by placing on a silicon wafer, heating from room temperature to 500° C. over a 3 hours period, holding at 500° C. for 2 hours, and cooling back to room temperature over a 3 hours period to obtain monodisperse porous silica spheres having an average diameter of 15 microns. These porous silica spheres having average diameter of 15 μm were porous silica microspheres. The average pore (void) diameter of the silica spheres was 170 nm and the average porosity was 0.8.

The drying step can be performed employing microwave irradiation, drying under vacuum and/or drying in the presence of a desiccant.

Example 2: Porous Silica Spheres Containing an Additional Light Absorber

The product of Example 1 was physically mixed with an aqueous dispersion of carbon black or with a carbon black powder at varying weight levels. Monodisperse porous silica spheres containing carbon black at levels of 0.5 weight-%, 1 weight-%, 2 weight-%, 3 weight-%, 4 weight-% and 5 weight-%, based on the total weight of the spheres were obtained.

Example 3: Porous Silica Spheres Via Spray-Drying

A styrene/acrylic acid copolymer was prepared as follows: 230 mL Deionized (DI) water was added to a 3-neck reaction flask equipped with a thermometer, condenser, magnetic stirring and nitrogen atmosphere. The water was heated to 80° C. and 10 g of styrene was added with stirring, followed by 100 mg acrylic acid dissolved in 10 mL DI water via syringe. 100 mg of ammonium persulfate was dissolved in 10 mL DI water and added to the stirred mixture via syringe. The reaction mixture was stirred for 24 hours at 80° C. The polymer colloid dispersion was allowed to cool to room temperature and was purified via centrifugation, producing polystyrene nanospheres having an average particle size of 250 nm.

The aqueous polystyrene colloid dispersion was diluted to 1 weight-% with deionized water and 1 weight-% silica nanoparticles were added and the mixture was sonicated to prevent particle agglomeration. The aqueous dispersion was spray-dried to provide polymer template spheres comprising polymer nanospheres and silica. The spheres are calcined by heating from room temperature to 500° C. over a 3 hours period, holding at 500° C. for 2 hours, and cooling back to room temperature over a 3 hours period to obtain porous silica spheres having an average diameter of 15 microns. The average pore (void) diameter of the silica spheres was 170 nm and the average porosity was 0.8.

Example 4: Porous Silica Spheres

A sample of porous silica spheres was prepared according to the procedure of example 3. The polymer nanospheres having an average particle size of 421 nm were used and a weight ratio of the polymer to silica was 3:1.

The silica spheres having an average diameter of 3.63 μm and an average pore (void) diameter of 368 nm were obtained. FIG. 1 shows SEM image of the porous silica sphere obtained according to example 4. The average porosity of the silica spheres was 0.8.

Example 5: Porous Silica Spheres

A sample of porous silica spheres was prepared according to the procedure of example 3. The polymer nanospheres having an average particle size of 421 nm were used and a weight ratio of the polymer to silica was 3:1.

Figure 2:
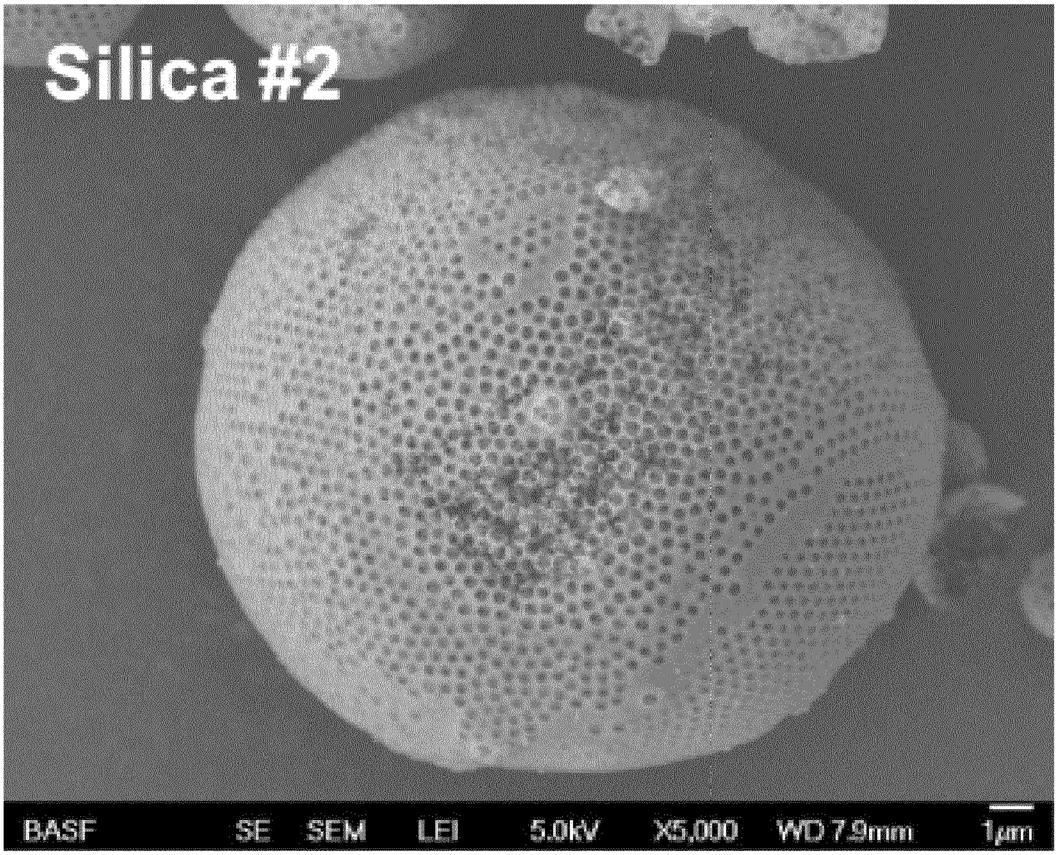
FIG. 2 is a SEM image of a porous silica sphere, according to an embodiment of the invention.

The silica spheres having an average diameter of 8.27 μm and pore (void) size an average pore (void) diameter of 365 nm were obtained. FIG. 2 shows SEM image of a porous silica sphere obtained according to example 5. The average porosity of the silica spheres was 0.8.

Example 6: Porous Zinc Oxide Spheres

A sample of porous zinc oxide spheres was prepared according to the procedure of Example 3, wherein silica was replaced with zinc oxide. The polystyrene nanospheres having an average diameter of 230 nm were used and a weight ratio of the polymer to zinc oxide was 1:2.

Example 7: Porous Titania Spheres

A sample of porous titania spheres was prepared according to the procedure of example 3, wherein silica was replaced with titania. The polymer nanospheres having an average particle size of 170 nm were used and a weight ratio of the polymer to titania was 3:1.

Figure 3:
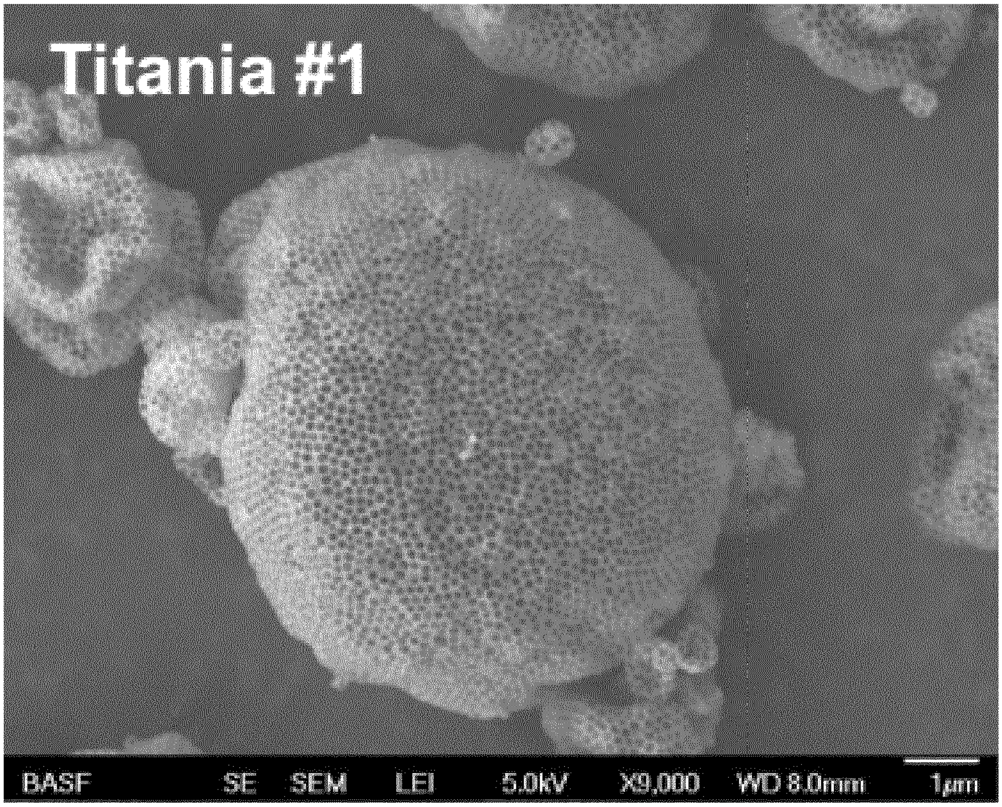
FIG. 3 is a SEM image of a porous titania sphere, according to an embodiment of the invention.

The titania spheres having an average diameter of 2.85 μm and an average pore (void) diameter of 142 nm were obtained. FIG. 3 shows SEM image of a porous titania sphere obtained according example 7. The average porosity of the titania spheres was 0.8.

Example 8: Porous Titania Spheres

Porous titania spheres were prepared by procedure similar to example 7. The polymer nanospheres having an average particle size of 285 nm were used and a weight ratio of the polymer to titania was 3:1.

Figure 4:
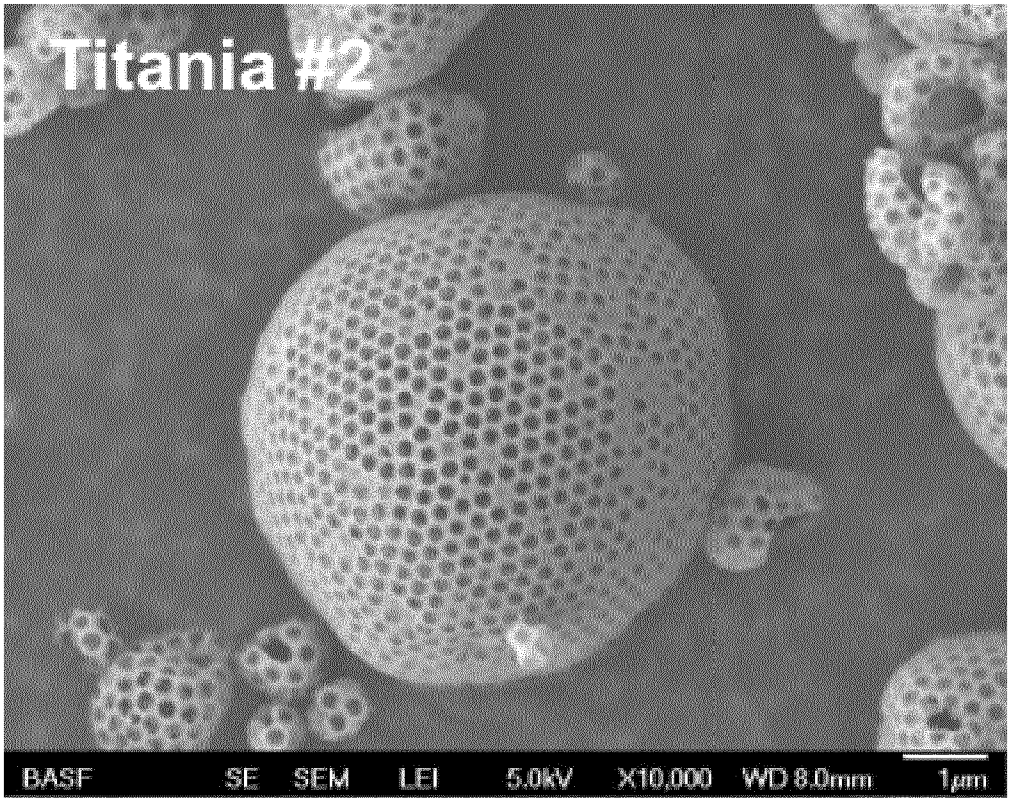
FIG. 4 is a SEM image of a porous titania sphere, according to an embodiment of the invention.

The titania spheres having an average diameter of 2.95 μm and an average pore (void) diameter of 243 nm were obtained. FIG. 4 shows SEM image of a porous titania sphere obtained according example 8. The average porosity of the titania spheres was 0.8.

Example 9: Porous Spheres Comprising Silica and Titania

Porous spheres containing silica and titania were prepared according to the process of Example 3, wherein the weight ratio of polymer to the total metal oxide was 3:1. The weight ratio of silica to titania was 9:1.

Example 10: Porous Spheres Having Two Average Particle Sizes

Step 1) Polymer spheres having at least two different average particle sizes: A styrene/acrylic acid copolymer was prepared as follows: 230 mL deionized (DI) water was added to a 3-neck reaction flask equipped with a thermometer, condenser, magnetic stirring and nitrogen atmosphere. The water was heated to 80° C. and 10 g of styrene was added with stirring, followed by 100 mg acrylic acid dissolved in 10 mL DI water via syringe. 100 mg of ammonium persulfate was dissolved in 10 mL DI water and added to the stirred mixture via syringe. The reaction mixture was stirred for 24 hours at 80° C. The polymer colloid dispersion was allowed to cool to room temperature and was purified via centrifugation, producing polystyrene nanospheres having an average particle size of 250 nm.

Similarly, a styrene/acrylic acid copolymer was prepared to produce polystyrene nanospheres having an average particle size of 350 nm.

The first aqueous polystyrene colloid dispersion (250 nm) was mixed with the second aqueous polystyrene colloid dispersion (350 nm) in a weight ratio of 7:3 and the mixture was diluted to 1 weight-% with deionized water and was sonicated to prevent particle agglomeration. The continuous oil phase used was 0.1 weight-% polyethylene glycol/perfluoropolyether surfactant in a fluorinated oil. The aqueous colloid dispersion mixture and oil were each injected into a microfluidic device having a 50 μm droplet junction via syringes associated with pumps. The system was allowed to equilibrate until monodisperse droplets were produced. The monodisperse droplets were collected in a reservoir.

Collected droplets were dried in an oven at 45° C. for 4 hours to provide monodisperse polymer spheres. The monodisperse polystyrene spheres comprise polystyrene nanospheres having a bimodal particle size distribution.

Step 2) Porous Metal Oxide Spheres

Example 1 was repeated, adding 1 weight-% silica nanoparticles to the aqueous mixture of first and second colloid dispersions prior to mixing with the oil phase to form a water-in-oil emulsion. The collected droplets from the microfluidic device were dried as in Example 1 to form polymer template spheres. The polymer template spheres were calcined by placing on a silicon wafer, heating from room temperature to 500° C. over a 3 hours period, holding at 500° C. for 2 hours, and cooling back to room temperature over a 3 hours period. Provided are monodisperse silica spheres having an average diameter of 15 microns, containing two different average pore sizes.

Example 11: Preparation of Porous Silica Spheres Having Two Average Particle Sizes Via Spray-Drying A styrene/acrylic acid copolymer was prepared as follows: 230 mL deionized (DI) water was added to a 3-neck reaction flask equipped with a thermometer, condenser, magnetic stirring and nitrogen atmosphere. The water was heated to 80° C. and 10 g of styrene are added with stirring, followed by 100 mg acrylic acid dissolved in 10 mL DI water via syringe. 100 mg of ammonium persulfate was dissolved in 10 mL DI water and added to the stirred mixture via syringe. The reaction mixture was stirred for 24 hours at 80° C. The polymer colloid dispersion was allowed to cool to room temperature and was purified via centrifugation, producing polystyrene nanospheres having an average particle size of 250 nm.

Similarly, a styrene/acrylic acid copolymer was prepared to produce polystyrene nanospheres having an average particle size of 350 nm.

The first aqueous polystyrene colloid dispersion (250 nm) was mixed with the second agueous polystyrene colloid dispersion (350 nm) in a weight ratio of 7:3 and the mixture was diluted to 1 weight-% with deionized water and 1 weight-% silica nanoparticles are added to the mixture which was sonicated to prevent particle agglomeration. The aqueous dispersion was spray-dried to provide polymer template spheres comprising monodisperse polymer nanospheres having bimodal distribution and silica. The spheres were calcined by heating from room temperature to 500° C. over a 3 hours period, holding at 500° C. for 2 hours, and cooling back to room temperature over a 3 hours period to obtain porous silica spheres.

Example 12: Porous Zinc Oxide Spheres Having Two Average Particle Sizes

A sample of porous zinc oxide spheres were prepared according to the process of Example 11, where the polystyrene nanospheres having average particle sizes of 250 nm and 320 nm were used in a weight ratio of 1:1, and where the weight ratio of the polymer to zinc oxide was 1:2.

Example 13: Porous Spheres Comprising Silica and Titania Having Two Average Particle Sizes A sample of porous spheres containing silica and titania was prepared according to the process of Example 11, where the polystyrene nanospheres have average particle sizes of 350 nm and 460 nm were used in a weight ratio of 1:4 and wherein the weight ratio of the polymer to total metal oxide was 3:1. The weight ratio of silica to titania was 9:1.

Determination of Properties

Experiment 1: Increase in the Absorbance of a Dye by Porous Silica Spheres

The porous microspheres comprising silica according to example 3 were dispersed in aqueous solutions of a water-soluble dye. The water-soluble dye was Patent Blue V (alternative name Acid Blue 3), its chemical name is 2-[(4- diethylaminophenyl)(4-diethylimino-2,5-cyclohexadien-1-ylidene)methyl]-4-hydroxy-1,5-benzene-disulfonate. It has molar decadic extinction coefficient of $\varepsilon$=113900 L $mol^{-1}$ $cm^{-1}$ at $\lambda_{max}$=637 nm.

Another aqueous dispersion containing the porous silica microspheres according to example 3 but not containing the dye, served as a reference sample.

The dispersions were filled into quartz cuvettes (Hellma Analytics) of 0.1 cm optical thickness and the absorbance was measured with a Perkin Elmer Lambda 20 UV/vis spectrometer having an integration sphere accessory (RSA-PE-20), which collected the direct transmitted light and also the light scattered in forward direction. Although the Perkin Elmer Lambda 20 is a double beam spectrometer, the integration sphere accessory is a single beam device.

Reference and sample dispersion cells were placed in the light beam at the transmittance port of the integration sphere, while a reflectance standard was mounted at the reflectance port of the sphere. Measurements were performed with a spectral resolution of 2 nm. First the absorbance of the reference dispersion was recorded and then that the corresponding sample was recorded.

Figure 5:
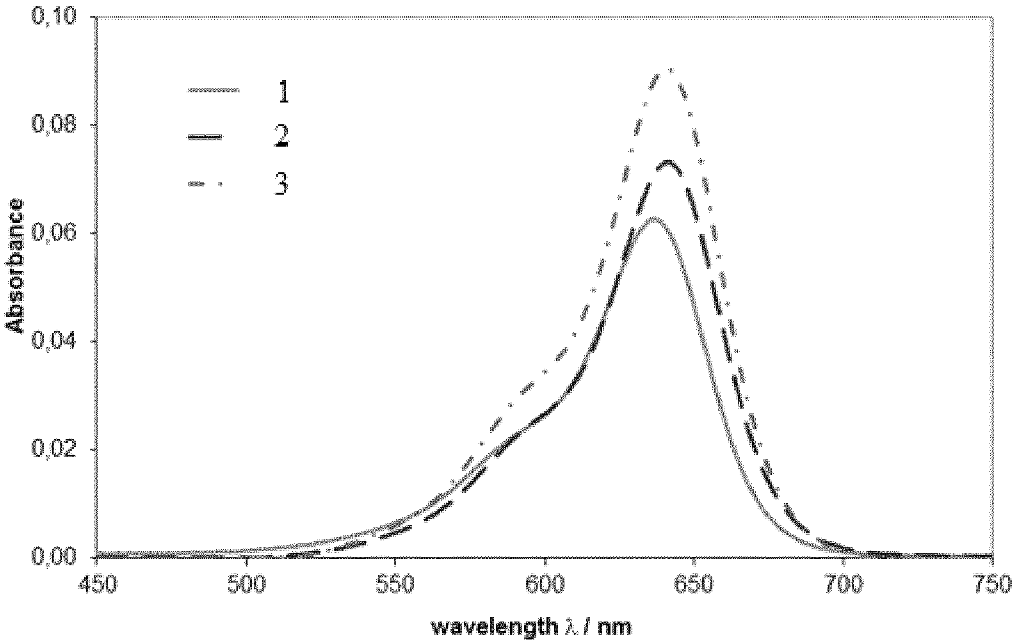
FIG. 5 depicts a graph related to absorbance of aqueous dispersions comprising Patent Blue V in the presence of porous silica spheres.

FIG. 5 shows the absorbance of aqueous dispersions comprising Patent Blue V at a constant concentration ($5.5 \cdot 10^{-6}$ mol/L) at an optical pathlength d of 0.1 cm in the presence of the porous silica spheres according to example 3. In FIG. 5, 1 refers to the absorption spectrum of reference sample; 2 refers to the absorption spectrum of aqueous dispersions comprising the porous silica spheres at a concentration of 2 wt %; and 3 refers to the absorption spectrum of aqueous dispersions comprising the porous silica spheres at a concentration of 5 wt %.

It is observed from FIG. 5 that the presence of porous silica spheres increases the efficacy of the dye absorbance, and the absorbance increases by a factor of about 1.5 at 5 weight-% porous microsphere concentration.

Experiment 2: Increase in the Absorbance of an UV Absorber by Porous Silica Spheres The procedure for experiment 2 was similar to that of experiment 1, except that a water-soluble UV-absorber Benzophenone-4 was used instead of Patent Blue V. The chemical name of this UV-absorber is 2-hydroxy-4-methoxybenzophenone-5-sulfonic acid. The molar decadic extinction coefficient of Benzophenone-4 is $\varepsilon$=13650 L $mol^{-1}$ $cm^{-1}$ at $\lambda_{max}$=286 nm.

Figure 6:
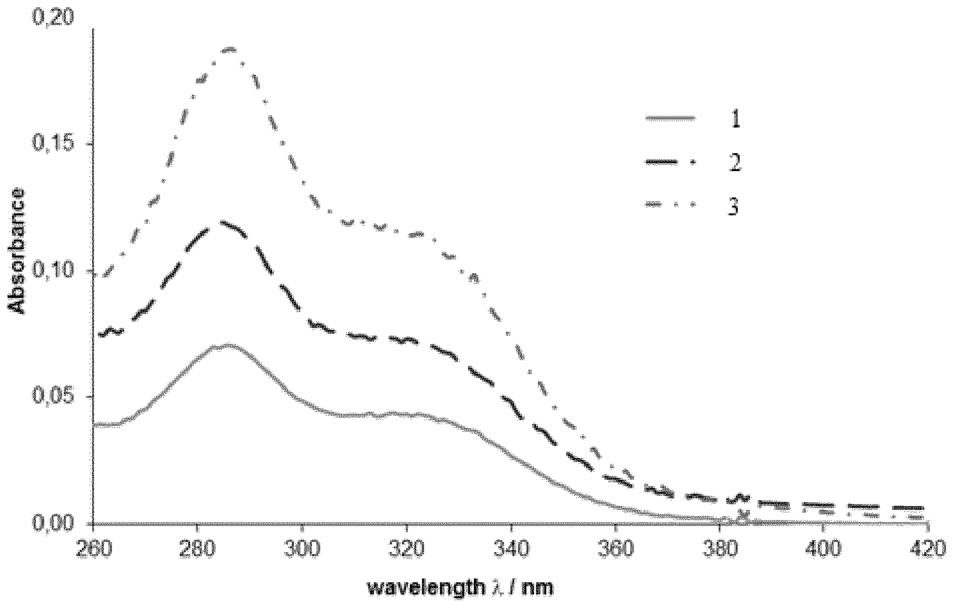
FIG. 6 depicts a graph related to UV absorbance of aqueous dispersions comprising benzophenone-4 in the presence of porous silica spheres.

FIG. 6 shows the absorbance of aqueous dispersions comprising Benzophenone-4 at a constant concentration of $5.18 \cdot 10^{5}$ mol/L, at an optical pathlength d of 0.1 cm in the presence of the porous silica spheres according to example 3. In FIG. 6, 1 refers to the absorption spectrum of reference sample; 2 refers to the absorption spectrum of aqueous dispersions comprising the porous silica spheres at a concentration of 2 wt %; and 3 refers to the absorption spectrum of aqueous dispersions comprising the porous silica spheres at a concentration of 5 wt %.

It is observed from FIG. 6 that the presence of porous silica spheres increases the efficacy of the UV absorbance of benzophenone-4, and the absorbance of UV radiations increases by a factor of about 2.5 at 5 wt % porous silica spheres concentration.

Thus, the boosting of absorbance, i.e. increase in the absorbance due to the presence of porous spheres, is greater in the UV range as compared to the visible range.

Experiment 3: Effect of Concentration on the UV Absorption

A set of five aqueous dispersions containing Benzophenone-4 and different concentrations of porous silica particles of example 3 was prepared by a procedure similar to experiment 2. Similarly, one set each of aqueous dispersion comprising different concentrations of porous silica particles of examples 4 and 5 each were prepared. A blank sample, which did not contain any porous metal oxide particles, was prepared for comparison. The UV absorbance was measured for the aqueous dispersions at the $\lambda_{max}$ of the UV absorber.

Figure 7:
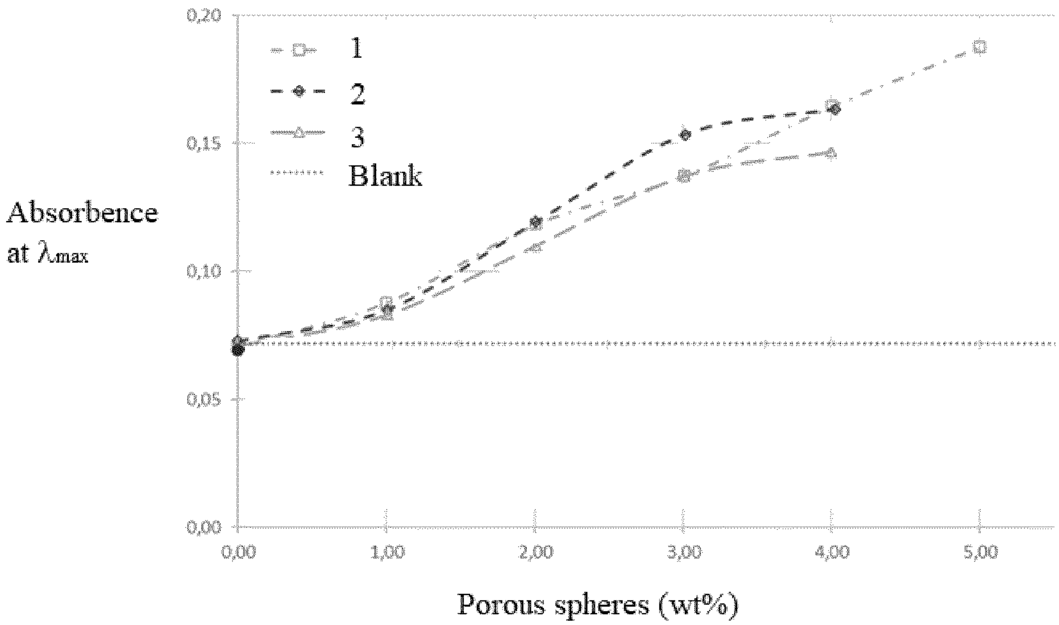
FIG. 7 depicts a graph related to UV absorbance $\lambda_{max}$ of aqueous dispersions comprising benzophenone-4 in the presence of varying amounts of porous silica spheres.

FIG. 7 shows a graph plotted for the absorbance of aqueous dispersions comprising Benzophenone-4 at an optical pathlength d of 0.1 cm at various concentrations of the porous silica spheres according to examples 3, 4 and 5. In FIG. 7, 1 refers to the absorption spectrum of aqueous dispersions comprising the porous silica spheres of example 3; 2 refers to the absorption spectrum of aqueous dispersions comprising the porous silica spheres of example 4; and 3 refers to the absorption spectrum of aqueous dispersions comprising the porous silica spheres of example 5; and blank refers to the absorbance of the blank sample.

It is observed from FIG. 7 that the efficacy of the UV absorbance of benzophenone-4 increases as the concentration of porous silica spheres increases.

Experiment 4: Comparative Example

A set of five aqueous dispersions containing Benzophenone-4 and different concentrations of the commercially available silica particles Sunsil® 130 from Sunjin was prepared by the procedure to experiment 2. A blank sample which did not contain the porous metal oxide particles was prepared for comparison. The UV absorbance was measured for the aqueous dispersions at the $\lambda_{max}$ of the UV absorber.

Figure 8:
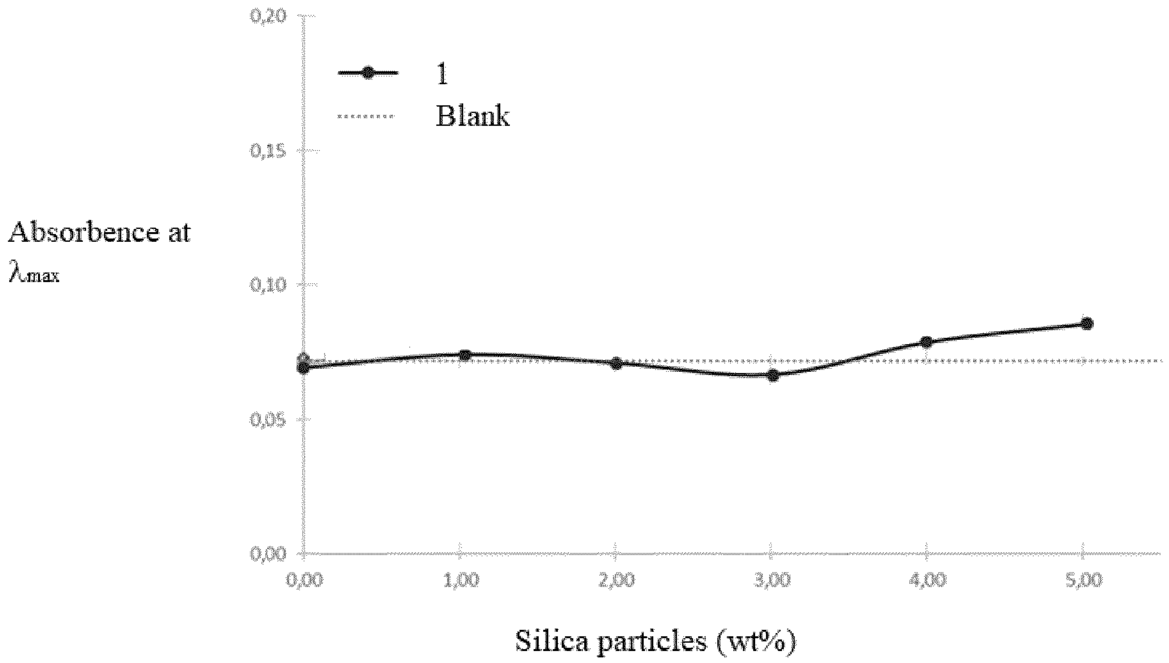
FIG. 8 depicts a graph related to UV absorbance $\lambda_{max}$ of aqueous dispersions comprising benzophenone-4 in the presence of commercial sample of Sunsil® 130.

FIG. 8 shows a graph plotted for the absorbance of aqueous dispersions comprising Benzophenone-4 at an optical pathlength d of 0.1 cm at various concentrations silica particles Sunsil® 130 at various concentrations. In FIG. 8, 1 refers to the absorption spectrum of aqueous dispersions comprising the Sunsil® 130 silica particles; and blank refers to the absorbance of the blank sample.

It is observed from FIG. 8 that the presence of silica particles Sunsil® 130 does not have any effect on the efficacy of the UV absorbance of Benzophenone-4.

Experiment 5: Increase in the Absorbance of a Dye by Porous Titania Spheres

The procedure of experiment 5 was similar to that of experiment 1, except that the porous silica particles were replaced by porous titania particles prepared according to examples 7 and 8.

Figure 9:
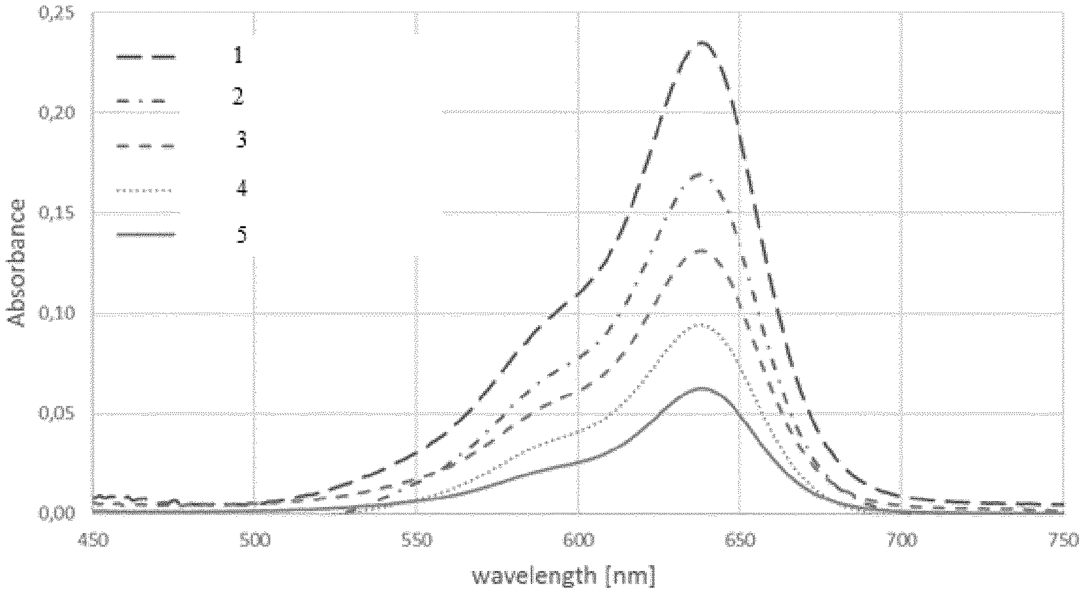
FIG. 9 depicts a graph related to absorbance of aqueous dispersions comprising Patent Blue V in the presence of porous titania spheres.

FIG. 9 shows the visible range absorption spectrum of the aqueous dispersions in the presence of the porous titania spheres according to examples 7 and 8 at a concentration of 0.2 wt % and 0.5 wt %, at an optical pathlength d of 0.1 cm. In FIG. 9, 1 refers to the absorption spectrum of aqueous dispersions comprising the porous titania spheres of example 8 at a concentration of 0.5 wt %; 2 refers to the absorption spectrum of aqueous dispersions comprising the porous titania spheres of example 7 at a concentration of 0.5 wt %; 3 refers to the absorption spectrum of aqueous dispersions comprising the porous titania spheres of example 8 at a concentration of 0.2 wt %; 4 refers to the absorption spectrum of aqueous dispersions comprising the porous titania spheres of example 7 at a concentration of 0.2 wt %; and 5 refers to the absorbance of the reference sample which do not contain any porous metal oxide spheres.

It is observed from FIG. 9 that the presence of porous titania spheres increases the efficacy of the dye absorbance, and the absorbance increases by a factor of about 2.8 and 4 at 5 weight-% porous microsphere concentration of the porous titania spheres from examples 7 and 8 respectively.

Experiment 6: Absorbance Spectra of Porous Titania Spheres

The porous titania spheres prepared according to examples 7 and 9 were dispersed in aqueous solutions which do not contain any dye or UV-absorber. The UV-absorption of these solutions was analysed in a manner similar to experiment 1.

Figure 10:
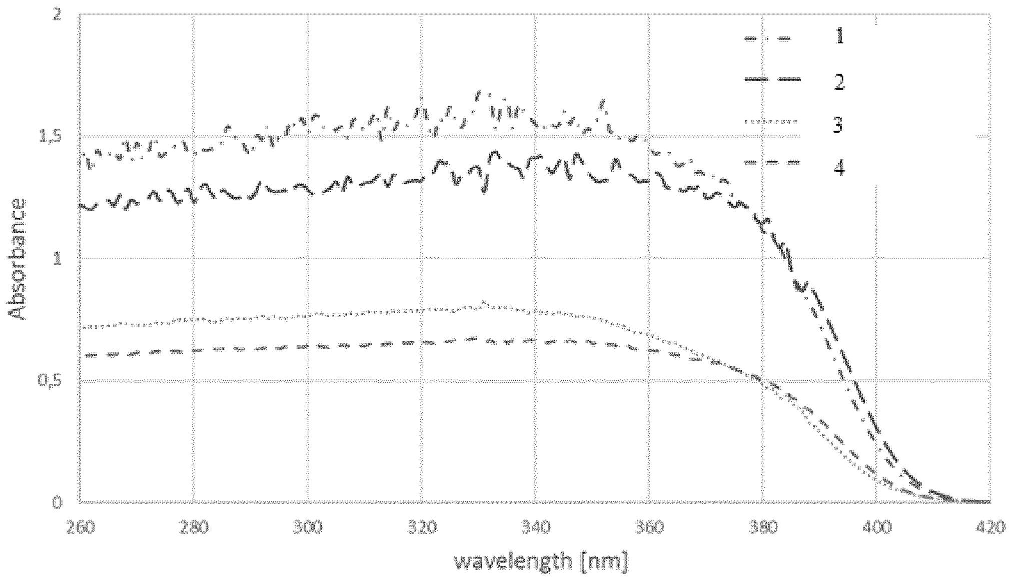
FIG. 10 depicts a graph related to UV absorbance of aqueous dispersions comprising porous titania spheres.

FIG. 10 shows the UV absorption spectrum of the aqueous dispersions comprising the porous titania spheres according to examples 7 and 8 at a concentration of 0.2 wt % and 0.5 wt % each, at an optical pathlength d of 0.1 cm. In FIG. 10, 1 refers to the absorption spectrum of aqueous dispersions comprising the porous titania spheres of example 7 at a concentration of 0.4 wt %; 2 refers to the absorption spectrum of aqueous dispersions comprising the porous titania spheres of example 8 at a concentration of 0.4 wt %; 3 refers to the absorption spectrum of aqueous dispersions comprising the porous titania spheres of example 7 at a concentration of 0.2 wt %; and 4 refers to the absorption spectrum of aqueous dispersions comprising the porous titania spheres of example 8 at a concentration of 0.2 wt %.

It is observed from FIG. 10 that the aqueous dispersion comprising porous titania spheres shows a broad UV absorbance in the range from 250 to 390 nm with the maximum UV absorbance in the range of 320 to 340 nm. The absorption is high in the UVB range of 290 to 320 nm, whereas the absorption shows a steep decrease in the UVA range of 380 to 420 nm.

Experiment 7: Sun Protection Factor (SPF) Experiments

For the determination of SPF, two sets of compositions were prepared. The first set of compositions were prepared with UV filters in the oil phase and the second set of compositions was prepared without additional UV filter.

3.1) Compositions with UV Filters

The following compositions were prepared:

TABLE 1

Formulations comprising UV filters

| Phase | Trade name | INCI | Basic composition | Composition 5 | Composition 6 | Placebo composition 8 | Reference Composition 9* for comparative analysis |
|---|---|---|---|---|---|---|---|
| A | Emulgade ® Sucro Plus | Sucrose Polystearate | 3.00 | 3.00 | 3.00 | 3.00 | 3.00 |
| | Eumulgin ® Prisma | Disodium Cetearyl Sulfosuccinate | 1.00 | 1.00 | 1.00 | 1.00 | 1.00 |
| | Lanette ® O | Cetearyl Alcohol | 2.00 | 2.00 | 2.00 | 2.00 | 2.00 |
| | Cetiol ® AB | Dicaprylyl Ether | 5.00 | 5.00 | 5.00 | 5.00 | 5.00 |
| | Cetiol ® Sensoft | Propylheptyl Caprylate | 5.00 | 5.00 | 5.00 | 5.00 | 5.00 |
| | Cetiol B | Dibutyl Adipate | 8.00 | 8.00 | 8.00 | 8.00 | 8.00 |
| | Euxyl ® PE 9010 | Phenoxyethanol and Ethylhexylglycerin | 1.00 | 1.00 | 1.00 | 1.00 | 1.00 |
| | Neoheliopan ® OS | Ethylhexyl Salicylate (EHS) | 5.00 | 5.00 | 5.00 | 5.00 | 5.00 |
| | Uvinul ® T 150 | Ethylhexyl Triazone (EHT) | 3.00 | 3.00 | 3.00 | 3.00 | 3.00 |
| | Uvinul ® A Plus | Diethylamino Hydroxybenzoyl Hexyl Benzoate (DHHB) | 5.00 | 5.00 | 5.00 | 5.00 | 5.00 |
| | Tinosorbe ® S | bis-ethylhexyloxyphenol methoxyphenyl triazine (BEMT) | 3.00 | 3.00 | 3.00 | 3.00 | 3.00 |
| B | Water | Aqua | 50.70 | 54.20 | 50.70 | 56.20 | 50.70 |
| | Glycerine | Glycerine | 2.00 | 2.00 | 2.00 | 2.00 | 2.00 |
| | Rheocare ® XGN | Xanthan Gum | 0.30 | 0.30 | 0.30 | 0.30 | 0.30 |
| | Cosmedia ® SP | | 0.50 | 0.50 | 0.50 | 0.50 | 0.50 |
| C | Porous microspheres according to Example 3 | | 0 | 2 | 5.5 | 0 | 0 |
| | Reference spheres | Sunspheres | 0 | 0 | 0 | 0 | 5.5 |

Procedure for preparation of a basic formulation: Phase A and phase B were separately heated with stirring. Phase A was incorporated to phase B under stirring. The mixture was stirred till a homogeneous mixture was obtained, followed by stirring for 1 min. Finally, the mixture is cooled under stirring to room temperature. The basic formulation was prepared at 80° C.

Sample Formulation:

Two formulations were prepared using 2 weight-% and 5.5 weight-% of porous spheres according to example 3 respectively. The porous spheres were incorporated under stirring in the basic formulation and filled up with water ad 100.

Reference formulation: The reference sample was prepared using the market product "SunSpheres®" from Dow Chemicals. The 5.5 weight-% of the market product was incorporated in the basic formulation. Sunspheres® are a styrene-acrylate copolymer with a hollow sphere morphology prepared via controlled emulsion polymerization.

Placebo formulation: The placebo sample without particles was prepared by adding water to the basic formulation ad 100.

Evaluation:

The SPF of these compositions was measured according to in vitro SPF method (according to R. M. Sayre et. al.) and the results are shown in Table 2.

TABLE 2

In vitro SPF evaluation of compositions comprising UV filters

| Composition | Composition 5 | Composition 6 | Placebo composition 8 | Reference Composition 9* for comparative analysis |
|---|---|---|---|---|
| Added particles | 2 weight-% porous microspheres according to example 3 | 5.5 weight-% porous microspheres according to example 3 | No particles | 5.5% Sunspheres ® |
| in vitro SPF (R. M. Sayre et. al.) | 101.3 | 107.4 | 84.1 | 132.4 |

Figure 11:
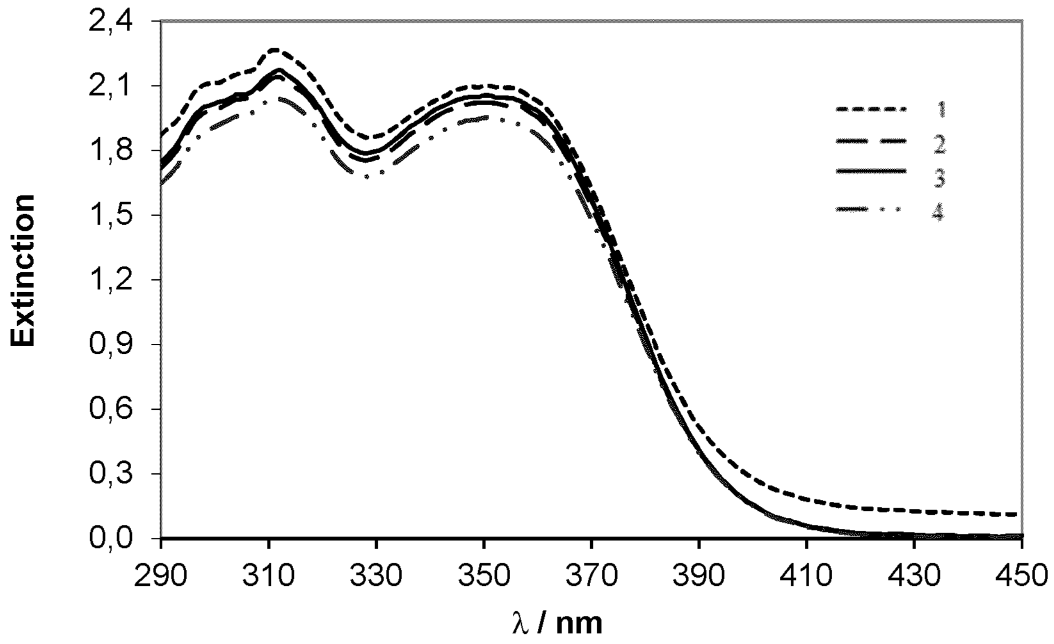
FIG. 11 depicts a graph related to the absorbance of sunscreen compositions comprising UV filters in the absence and the presence of porous silica spheres.

FIG. 11 shows the absorbance of the compositions 5, 6, 8 and 9 in the wavelength range of 290 to 450 nm. In FIG. 11, 1 refers to the absorption spectrum of composition 9; 2 refers to the absorption spectrum of composition 5; 3 refers to the absorption spectrum of composition 6; and 4 refers to the absorption spectrum of placebo composition 8.

The in vitro SPF increases with the addition of 2% porous silica spheres by 20%, and the in vitro SPF even increases by 28% with the addition of 5,5% porous silica spheres. It can be concluded, that the presence of porous spheres increases the efficacy of the UV absorbance, at 5,5% particle concentration by a factor of about 6.6 at 312 nm (UVB peak maximum) and by a factor of about 5.3 at 351 nm (UVA peak maximum).

An increase in SPF was also observed in the composition comprising Sunspheres® for comparative analysis. However, the nano-particulate character of Sunspheres® can be recognized by the scattering fraction at higher wavelengths above 400 nm commonly referred to as "tailing". This scattering leads to an undesired visible whitening effect on the skin.

3.2) Formulations without an Additional UV Filter

The following formulations were prepared using the procedure mentioned herein above in experiment 3.1. The content of basic and reference compositions is provided in Table 3.

TABLE 3

Basic and reference compositions without an additional UV filter

| | Trade name | INCI | Basic | Placebo |
|---|---|---|---|---|
| A | Emulgade ® Sucro | Sucrose Polystearate (and) Hydrogenated Polyisobutene | 3.00 | 3.00 |
| | Eumulgin ® Prisma | Disodium Cetearyl Sulfosuccinate | 1.00 | 1.00 |
| | Cetiol ® B | Dibutyl Adipate | 10.00 | 10.00 |
| | Dub DIS | Diisopropyl Sebacate | 4.00 | 4.00 |
| | Lanette ® O | Cetearyl Alcohol | 1.00 | 1.00 |
| B | Water | Aqua | 68.3 | 76.30 |
| | Glycerin | Glycerin | 3.00 | 3.00 |
| | EDTA BD | Disodium EDTA | 0.20 | 0.20 |
| | Keltrol ® RD | Xanthan Gum | 0.50 | 0.50 |
| | Protectol ® PE | Phenoxyethanol | 1.00 | 1.00 |

Placebo Formulation:

The placebo sample without particles was prepared by adding water to the basic formulation ad 100.

Sample Formulation:

Three formulations were prepared using 2 weight-%, 5.5 weight-% and 8-weight % of porous silica spheres according to example 3, respectively. The porous spheres were incorporated with water in the basic formulation.

Reference formulation: The reference sample was prepared using the market product "Sun-Spheres®" from Dow Chemicals. The 5.5 weight-% the market product was incorporated in the basic formulation.

TABLE 4

Formulations without an additional UV filter

| | Trade name | INCI | Composition 1 | Composition 2 | Composition 3 | Reference Composition 4* for comparative analysis |
|---|---|---|---|---|---|---|
| A | Emulgade ® Sucro | Sucrose Polystearate (and) Hydrogenated Polyisobutene | 3.00 | 3.00 | 3.00 | 3.00 |
| | Eumulgin ® Prisma | Disodium Cetearyl Sulfosuccinate | 1.00 | 1.00 | 1.00 | 1.00 |
| | Cetiol ® B | Dibutyl Adipate | 10.00 | 10.00 | 10.00 | 10.00 |
| | Dub DIS | Diisopropyl Sebacate | 4.00 | 4.00 | 4.00 | 4.00 |
| | Lanette ® O | Cetearyl Alcohol | 1.00 | 1.00 | 1.00 | 1.00 |
| B | Water* | Aqua | 74.3 | 70.8 | 68.3 | 70.8 |
| | Glycerin | Glycerin | 3.00 | 3.00 | 3.00 | 3.00 |
| | EDTA BD | Disodium EDTA | 0.20 | 0.20 | 0.20 | 0.20 |
| | Keltrol ® RD | Xanthan Gum | 0.50 | 0.50 | 0.50 | 0.50 |
| | Protectol ® PE | Phenoxyethanol | 1.00 | 1.00 | 1.00 | 1.00 |
| C | Particle | Porous microspheres according to example 3 | 2 | 5.5 | 8 | 0 |
| | Particle | SunSpheres ® | 0 | 0 | 0 | 5.5 |

The SPF of these compositions was measured according to in vitro SPF method (according to R. M. Sayre et. al.) and the results are shown in Table 5.

TABLE 5

In vitro SPF evaluation of samples without additional UV absorber

| Composition | Placebo | Composition 1 | Composition 2 | Composition 3 | Reference Composition 4* for comparative analysis |
|---|---|---|---|---|---|
| Added particles | No particles | 2 weight-% Porous microspheres according to example 3 | 5.5 weight-% Porous microspheres according to example 3 | 8 weight-% Porous microspheres according to example 3 | 5.5 weight-% Sunspheres ® |
| in vitro SPF (R. M. Sayre et. al.) | 1.1 | 1.1 | 1.2 | 1.3 | 1.5 |

Figure 12:
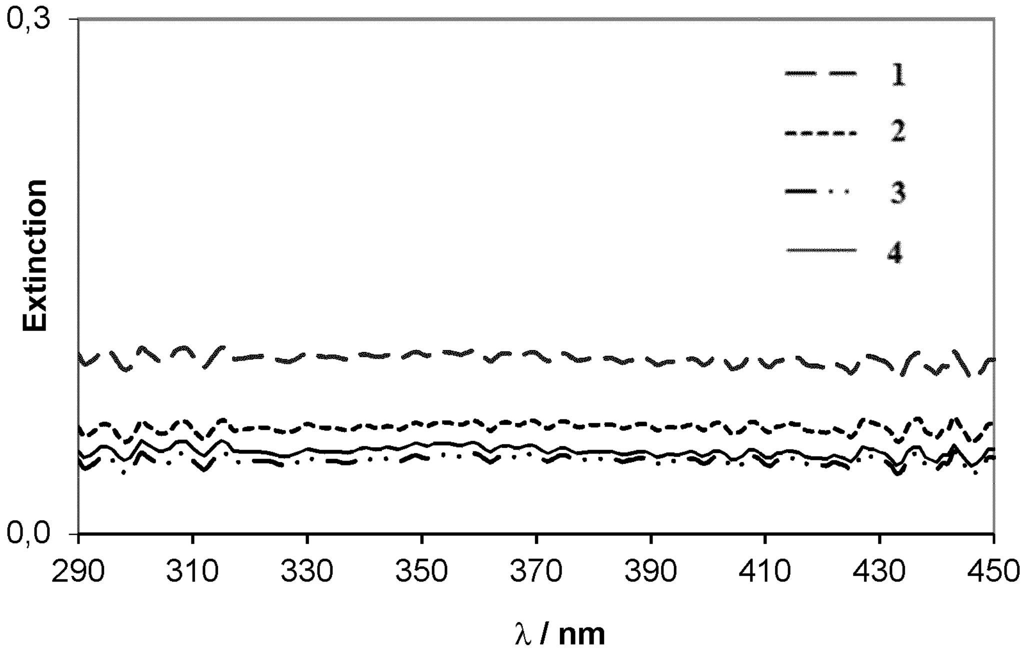
FIG. 12 depicts a graph related to the absorbance of sunscreen compositions without an additional UV filter in the absence and the presence of porous silica spheres.

FIG. 12 shows the absorbance of the compositions without an additional UV filter in the range from 290 to 450 nm. In FIG. 12, 1 refers to the absorption spectrum of composition 3; 2 refers to the absorption spectrum of composition 2; 3 refers to the absorption spectrum of composition 1; and 4 refers to the absorption spectrum of placebo composition.

The compositions with 5,5 weight-% or 8 weight-% of added particles show increased absorption over the whole UV range from 290 to 450 nm. The in vitro SPF of the composition could be increased by 10% with addition of 5,5 weight-% of porous spheres according to example 3 and by 20% with addition of 8 weight-% of porous spheres according to example 3.

Experiment 4: Transparency/Whitening Experiments

The whitening data were determined for both formulation series prepared in experiment 3 by color measurement as described above.

Figure 13:
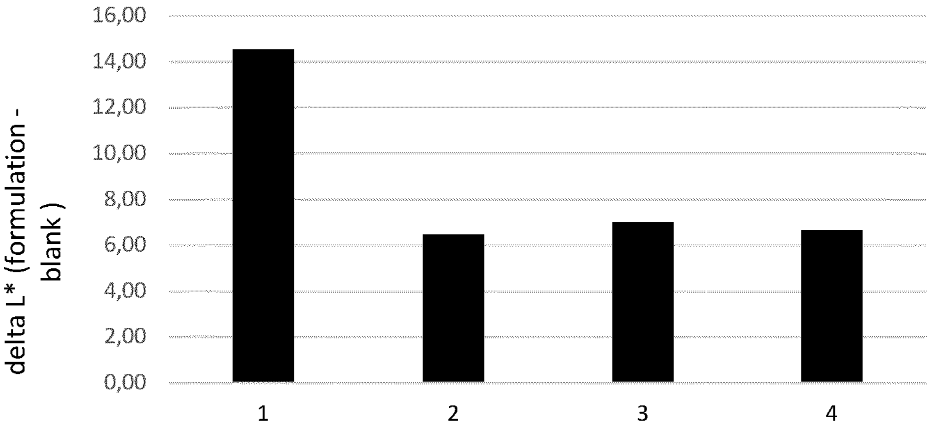
FIG. 13 depicts a chart related to the whitening effect of sunscreen compositions comprising UV filters in the absence and the presence of porous silica spheres.

The results for formulations with UV-filters are summarized in FIG. 13. In FIG. 13, 1 refers to the absorption spectrum of composition 9; 2 refers to the absorption spectrum of composition 5; 3 refers to the absorption spectrum of composition 6; and 4 refers to the absorption spectrum of placebo composition 8.

Figure 14:
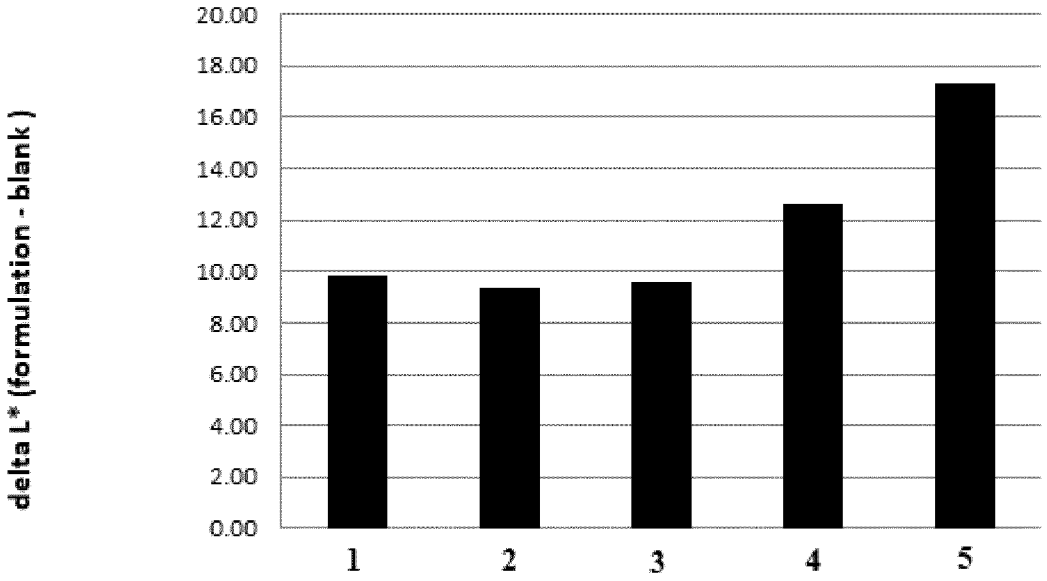
FIG. 14 depicts a chart related to the whitening effect of sunscreen compositions without an additional UV filter in the absence and the presence of porous silica spheres.

The results for formulations without UV-filters are summarized in FIG. 14. In FIG. 14, 1 refers to the absorption spectrum of placebo composition; 2 refers to the absorption spectrum of composition 1; 3 refers to the absorption spectrum of composition 2; 4 refers to the absorption spectrum of composition 3; and 5 refers to the absorption spectrum of composition 4 containing the reference composition.

It is observed from FIG. 13 and FIG. 14 that the "Sunspheres®" scatter the visible light significantly and thus produce strong whitening effect on the skin. Delta L* increases by 8 (120%) in FIG. 13 and by 7.5 (77%) in FIG. 14. In contrary the porous spheres of the present invention do not produce this whitening effect. The brightness of the formulations comprising the porous spheres of the present invention is the same as the brightness of the reference. Only with the highest concentration of 8 weight-% of porous spheres a slight increase by 2,8 (29%) is observed which is not visible, because only differences of delta L* greater than 4 can be recognized by the untrained human eye.

The invention claimed is:

1. A method for increasing the sun protection factor of a sunscreen composition, the method comprising adding porous spheres comprising a metal oxide to the sunscreen composition, wherein the metal oxide is at least one selected from the group consisting of silica, titania, alumina, zirconia, ceria, iron oxides, zinc oxide, indium oxide, tin oxide and chromium oxide: wherein the porous spheres have a uniform pore diameter with an average pore diameter in the range of 50 nm to 999 nm; wherein the porous spheres have an average diameter in the range of 0.5 μm to 100.0 μm; and wherein the method further minimizes or masks the whitening effect of the sunscreen composition and maintains its transparency.

2. The method according to claim 1, wherein the porous spheres are present in an amount in the range of 0.1 to 10.0 weight-%, based on total weight of the sunscreen composition.

3. The method according to claim 1, wherein the amount of the metal oxide in the porous spheres is in the range of 60.0 to 99.9 weight-%, based on total weight of the porous spheres.

4. The method according to claim 1, wherein the porous spheres have an average porosity in the range of 0.10 to 0.90.

5. The method according to claim 1, wherein the porous spheres have an average porosity in the range of 0.10 to 0.80.

6. The method according to claim 1, wherein the porous spheres are monodisperse.

7. The method according to claim 1, wherein the porous spheres have more than one population of pores each having an average pore diameter, wherein each population has a different average pore diameter.

8. The method or use according to claim 1, wherein the porous spheres have an average porosity in the range of 0.10 to 0.90; and are monodisperse.

9. The method according to claim 1, wherein the porous spheres have an average porosity in the range of 0.10 to 0.80; and are monodisperse.

10. The method according to claim 1, wherein the sunscreen composition further comprises an UV absorber selected from the group consisting of ($d_1$) p-aminobenzoic acid derivatives;

($d_2$) salicylic acid derivatives;

($d_3$) benzophenone derivatives;

($d_4$) dibenzoylmethane derivatives;

($d_5$) diphenyl acrylates;

($d_6$) 3-imidazol-4-yl-acrylic acid and its esters;

($d_7$) benzofuran derivatives;

($d_8$) polymeric UV absorbers;

($d_9$) cinnamic acid derivatives;

($d_{10}$) camphor derivatives;

($d_{11}$) hydroxyphenyltriazine derivatives;

($d_{12}$) benzotriazole derivatives;

($d_{13}$) trianilino-s-triazine derivatives;

($d_{14}$) 2-phenylbenzimidazole-5-sulfonic acid and salts thereof;

($d_{15}$) menthyl o-aminobenzoates;

($d_{16}$) homosalates;

($d_{17}$) tris-biphenyltriazine derivatives;

($d_{18}$) $TiO_2$ (partly encapsulated), ZnO and mica;

($d_{19}$) benzylidenemalonates;
($d_{20}$) merocyanine derivatives;
($d_{21}$) phenylene bis diphenyltriazines;
($d_{22}$) imidazoline derivatives; and
($d_{23}$) diarylbutadiene derivatives.

11. The method according to claim 1, wherein the method further minimizes or masks the whitening effect of the sunscreen composition and maintains its transparency.

12. The use according to claim 1, wherein the use further minimizes or masks the whitening effect of the sunscreen composition and maintains its transparency.

13. The method according to claim 1, wherein the porous spheres have an average diameter in the range of 10.0 μm to 50.0 μm.

14. The method according to claim 1, wherein the porous spheres have a uniform pore diameter with an average pore diameter in the range of 100 nm to 600 nm.

15. The method according to claim 14, wherein the metal oxide is silica.

* * * * *